United States Patent
Castro-Palomino Lária et al.

(10) Patent No.: US 10,238,637 B2
(45) Date of Patent: Mar. 26, 2019

(54) MODULATORS OF THE ADENOSINE A3 RECEPTORS

(71) Applicant: PALOBIOFARMA, S.L., Mataro, Barcelona (ES)

(72) Inventors: Julio Castro-Palomino Lária, Barcelona (ES); Juan Camacho Gómez, Barcelona (ES)

(73) Assignee: PALOBIOFARMA, S.L., Mataro, Barcelona (ES)

( * ) Notice: Subject to any disclaimer, the term of this patent is extended or adjusted under 35 U.S.C. 154(b) by 0 days.

(21) Appl. No.: 15/544,429

(22) PCT Filed: Jan. 22, 2016

(86) PCT No.: PCT/ES2016/070032
§ 371 (c)(1),
(2) Date: Jul. 18, 2017

(87) PCT Pub. No.: WO2016/116652
PCT Pub. Date: Jul. 28, 2016

(65) Prior Publication Data
US 2018/0263963 A1    Sep. 20, 2018

(30) Foreign Application Priority Data
Jan. 22, 2015  (ES) .................. 201530085

(51) Int. Cl.
| | | |
|---|---|---|
| *C07D 277/32* | (2006.01) | |
| *C07D 277/38* | (2006.01) | |
| *A61K 31/426* | (2006.01) | |
| *A61K 31/427* | (2006.01) | |
| *C07D 233/56* | (2006.01) | |
| *C07D 417/12* | (2006.01) | |
| *C07D 417/14* | (2006.01) | |
| *A61P 27/06* | (2006.01) | |
| *A61P 11/06* | (2006.01) | |
| *A61P 19/02* | (2006.01) | |
| *A61P 13/12* | (2006.01) | |
| *A61P 35/00* | (2006.01) | |
| *A61K 31/454* | (2006.01) | |
| *A61K 31/167* | (2006.01) | |
| *A61K 31/277* | (2006.01) | |
| *A61K 31/352* | (2006.01) | |
| *A61K 31/47* | (2006.01) | |
| *A61K 31/519* | (2006.01) | |
| *A61K 31/549* | (2006.01) | |

(52) U.S. Cl.
CPC .......... *A61K 31/426* (2013.01); *A61K 31/427* (2013.01); *A61K 31/454* (2013.01); *A61P 11/06* (2018.01); *A61P 13/12* (2018.01); *A61P 19/02* (2018.01); *A61P 27/06* (2018.01); *A61P 35/00* (2018.01); *C07D 233/56* (2013.01); *C07D 417/12* (2013.01); *C07D 417/14* (2013.01); *A61K 31/167* (2013.01); *A61K 31/277* (2013.01); *A61K 31/352* (2013.01); *A61K 31/47* (2013.01); *A61K 31/519* (2013.01); *A61K 31/549* (2013.01); *A61K 2300/00* (2013.01)

(58) Field of Classification Search
USPC .......... 548/190, 198; 546/209; 514/326, 371
See application file for complete search history.

(56) References Cited

U.S. PATENT DOCUMENTS

| | | |
|---|---|---|
| 6,303,619 B1 | 10/2001 | Linden |
| 6,407,236 B1 | 6/2002 | Baraldi et al. |
| 6,673,802 B2 | 1/2004 | Castelhano et al. |
| 6,686,366 B1 | 2/2004 | Castelhano et al. |

(Continued)

FOREIGN PATENT DOCUMENTS

| | | |
|---|---|---|
| EP | 1180518 A1 | 2/2002 |
| ES | 2204262 A1 | 4/2004 |

(Continued)

OTHER PUBLICATIONS

Borghini, Alice, et al.; "QSAR study on thiazole and thiadiazole analogues as antagonists for the adenosine A1 and A3 receptors," Bioorganic & Medicinal Chemistry, 2005, pp. 5330-5337, vol. 13.

(Continued)

*Primary Examiner* — Nyeemah A Grazier
(74) *Attorney, Agent, or Firm* — Tristan A. Fuierer; Olive Law Group, PLLC

(57) ABSTRACT

Modulators of adenosin $A_3$ receptors of formula (I):

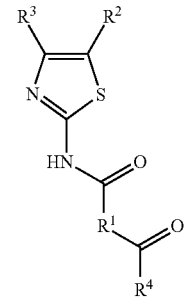

And procedure for preparing these compounds. Other objectives of the present invention are to provide pharmaceutical compositions comprising an effective amount of these compounds and the use of the compounds for manufacturing a medicament for the treatment of pathological conditions or diseases that can improve by modulation of the adenosine $A_3$ receptor.

14 Claims, No Drawings

(56) References Cited

U.S. PATENT DOCUMENTS

| | | | |
|---|---|---|---|
| 6,969,723 | B2 | 11/2005 | Aranyl et al. |
| 7,176,213 | B2 | 2/2007 | Aranyl et al. |
| 2003/0203897 | A1 | 1/2003 | Love et al. |
| 2010/0311703 | A1* | 12/2010 | Gonzalez Lio ...... C07D 417/04 514/171 |
| 2011/0171130 | A1 | 7/2011 | Jacobson et al. |
| 2011/0190324 | A1 | 8/2011 | Leung |
| 2012/0053176 | A1 | 3/2012 | Armstrong et al. |
| 2012/0134945 | A1 | 5/2012 | Madi et al. |

FOREIGN PATENT DOCUMENTS

| | | |
|---|---|---|
| ES | 2360632 T3 | 6/2011 |
| ES | 2366075 T3 | 10/2011 |
| WO | 9921555 A2 | 5/1999 |
| WO | 9964418 A1 | 12/1999 |
| WO | 0003741 A2 | 1/2000 |
| WO | 0015231 A1 | 3/2000 |
| WO | 2005009969 A1 | 2/2005 |
| WO | 2007089507 A1 | 8/2007 |
| WO | 2007116106 A1 | 10/2007 |
| WO | 2008006369 A1 | 1/2008 |
| WO | 2008045330 A2 | 4/2008 |
| WO | 2008124000 A2 | 10/2008 |
| WO | 2009044250 A1 | 4/2009 |
| WO | 2009052310 A1 | 4/2009 |

OTHER PUBLICATIONS

Bhattacharya, Prosenjit, et al.; "Exploring QSAR of thiazole and thiadiazole derivatives as potent and selective human adenosine A3 receptor antagonists using FA and GFA techniques," Bioorganic & Medicinal Chemistry, 2005, pp. 1159-1165, vol. 13.

Van Muijlwijk-Koezen, Jacqueline E., et al.; "Thiazole and Thiadiazole Analogues as a Novel Class of Adenosine Receptor Antagonists," J. Med. Chem. 2001, pp. 749-762, vol. 44.

Inamdar, Gajanan S., et al.; "New insight into adenosine receptors selectivity derived from a novel series of [5-substituted-4-phenyl-1,2-thiazol-2-yl] benzamides and furamides," European Journal of Medicinal Chemistry, 2013, 63. 924-934.

International Search Report, dated Apr. 1, 2016.

Hanauer, S.B., et al.; "The state of the art in the management of inflammatory bowel disease," Rev. Gastroenterol. Disord., 2003, vol. 3, pp. 81-92.

De Schepper, H.U., et al.; "Review article: gastrointestinal sensory and motor disturbances in inflammatory bowel disease: clinical relevance and pathophysiological mechanisms," Aliment. Pharmacol. Ther., 2008, vol. 27, pp. 621-637.

Ochaion, A et al.; "The anti-inflammatory target A(3) adenosine receptor is over-expressed in rheumatoid arthritis, psoriasis and Crohn's disease," Cell Immunol., 2009; vol. 25, pp. 115-122. doi: 10.1016/j.cellimm.2009.03.020. Epub May 7, 2009.

Mabley, J., et al.; "The adenosine A3 receptor agonist, N6-(3-iodobenzyl)-adenosine-5'-N-methyluronamide, is protective in two murine models of colitis," Eur. J. Pharmacol, 2003, vol. 466, pp. 323-329.

Ren, T, MD, PHD, et al.; "Impact of Disrupting Adenosine A3 Receptors (A3-/-AR) on Colonic Motility or Progression of Colitis in the Mouse," Inflamm Bowel Dis., Aug. 2011; vol. 17, pp. 1698-1713. doi:10.1002/ibd.21553.

Butler, M, et al.; "Impairment of adenosine A3 receptor activity disrupts neutrophil migratory capacity and impacts innate immune function in vivo," European Journal of Immunology, 2012, doi: 10.1002/eji.201242655.

Boison, D., "Adenosine as a modulator of brain activity," Drug News Perspect, 2007, vol. 20, pp. 607-611; Abstract Only.

Burnstock, G., et al.; "Adenosine and ATP receptors in the brain," Curr. Top. Med. Chem., 2011, vol. 11, pp. 973-1011.

Yoon, M.N., et al.; "Roles of adenosine receptor subtypes in the antinociceptive effect of intrathecal adenosine in a rat formalin test," Pharmacology, 2006, vol. 78, pp. 21-26.

Pugliese, A.M., et al.; "Brief, repeated, oxygen-glucose deprivation episodes protect neurotransmission from a longer ischemic episode in the in vitro hippocampus: role of adenosine receptors," Br. J. Pharmacol., 2003, vol. 140, pp. 305-314.

Von Arnim, C.A., et al.; "GGA1 acts as a spatial switch altering amyloid precursor protein trafficking and processing," J. Neurosci., 2006, vol. 26, pp. 9913-9922.

Koscsó, B et al.; "Investigational A3 adenosine receptor targeting agents," Expert Opin Investig Drugs, 2011; vol. 20, pp. 757-768. doi:10.1517/13543784.2011.573785.

Lee, Thomas, H et al. "A3 adenosine receptor knockout mice are protected against ischemia- and myoglobinuria-induced renal failure" Am J Physiol Renal Physiol, 2003, vol. 284, pp. F267-F273.

Maddock, H.L., et al.; "Adenosine A3 receptor activation protects the myocardium from reperfusion/ reoxygenation injury", Am. J. Physiol.: Heart Circ. Physiol, 2002, vol. 283, pp. H1307-H1313.

Gessi, S., et al.; "Adenosine modulates HIF-1{alpha}, VEGF, IL-8, and foam cell formation in a human model of hypoxic foam cells," Arterioscler., Thromb., Vasc. Biol., 2010, vol. 30, pp. 90-97.

Van Der Hoeven, D., et al.; "Activation of the A3 adenosine receptor suppresses superoxide production and chemotaxis of mouse bone marrow neutrophils," Mol. Pharmacol, 2008, vol. 74, pp. 685-696.

Salvatore, C.A., et al.; "Disruption of the A3 adenosine receptor gene in mice and its effect on stimulated inflammatory cells," J. Biol.Chem., 2000, vol. 275, pp. 4429-4434.

Zhong, H., et al.; , H.; "Activation of murine lung mast cells by the adenosine A3 receptor," J. Immunol., 2003, vol. 171, pp. 338-345.

Young, H. W., et al.; "A3 adenosine receptor signaling contributes to airway inflammation and mucus production in adenosine deaminase-deficient mice," J. Immunol., 2004, vol. 173, pp. 1380-1389.

Silverman, M.H., et al.; "Clinical evidence for utilization of the A3 adenosine receptor as a target to treat rheumatoid arthritis: data from a phase II clinical trial," J. Rheumatol., 2008, vol. 35, pp. 41-48.

Bar-Yehuda, S., et al; "The anti-inflammatory effect of A3 adenosine receptor agonists: a novel targeted therapy for rheumatoid arthritis," Expert Opin. Invest. Drugs, 2007, vol. 16, pp. 1601-1613.

Zhong, Y. et al., "Adenosine, adenosine receptors and glaucoma: An updated overview," Biochim. Biophys. Acta, 2013; 1830, 2882-2890.

Yang, H.et al.; "The cross-species adenosine-receptor antagonist MRS 1292 inhibits adenosine-triggered human nonpigmented ciliary epithelial cell fluid release and reduces mouse intraocular pressure," Curr. Eye Res., 2005, vol. 30, pp. 747-754.

Schlotzer-Schrehardt, U., et al.; "Selective upregulation of the A3 adenosine receptor in eyes with pseudoexfoliation syndrome and glaucoma," Invest. Ophthalmol. Visual Sci., 2005, vol. 46, pp. 2023-2034.

Zhang, M., et al.; "The A3 adenosine receptor attenuates the calcium rise triggered by NMDA receptors in retinal ganglion cells," Neurochem. Int., 2010, vol. 56, pp. 35-41.

Bar-Yehuda, S., et al.; "Inhibition of experimental auto-immune uveitis by the A3 adenosine receptor agonist CF101," Int. J. Mol. Med., 2011, vol. 28, pp. 727-731.

Gessi, S., et al.; "Adenosine receptors in colon carcinoma tissues and colon tumoral cell lines: focus on the A3 adenosine subtype," J. Cell. Physiol., 2007, vol. 211, pp. 826-836.

Jajoo, S., et al.; "Adenosine A3 receptor suppresses prostate cancer metastasis by inhibiting NADPH oxidase activity," Neoplasia, 2009, vol. 11, pp. 1132-1145.

Stoilov, R., et al.; "Therapeutic Effect of Oral CF101 in Patients with Rheumatoid Arthritis: A Randomized, Double-blind, Placebo-controlled Phase II Study," Immunome Research, 2014, vol. 11; 087. doi: 10.4172/17457580.1000087.

Ochoa-Cortes, Fernando, et al.; "Potential for Developing Purinergic Drugs for Gastrointestinal Diseases," Inflamm Bowel Dis, 2014, pp. 1259-1287, vol. 20.

Rybaczyk, Leszek, et al.; "New Bioinformatics Approach to Analyze Gene Expressions and Signaling Pathways Reveals Unique Purine Gene Dysregulation Profiles that Distinguish Between CD and UC," Inflamm Bowel Dis, 2009, pp. 971-984, vol. 15.

(56) References Cited

OTHER PUBLICATIONS

Trincavelli, Maria Letizia, et al.; "Agonist-Induced Internalization and Recycling of Human A3 Adenosine Receptors: Role in Receptor Desensitization and Resensitization," Journal of Neurochemistry, 2000, pp. 1493-1501, vol. 75.

Ali, Faisal R., et al.; "Psoriasis and Susceptibility to Other Autoimmune Diseases," Expert Rev Clin Immunol., 2013, pp. 99-101, vol. 9.

* cited by examiner

MODULATORS OF THE ADENOSINE A3 RECEPTORS

CROSS-REFERENCE TO RELATED APPLICATIONS

This application is filed under the provisions of 35 U.S.C. § 371 and claims the priority of International Patent Application No. PCT/ES2016/070032 filed on 22 Jan. 2016 entitled "MODULATORS OF THE ADENOSINE $A_3$ RECEPTORS" in the name of Julio CASTRO-PALOMINO LÁRIA, et al., which claims priority to Spanish Patent Application No. P201530085, filed on 22 Jan. 2015, both of which are hereby incorporated by reference herein in their entirety.

DESCRIPTION

Field of the Invention

The present invention relates 2-amido-1,3-thiazole derivatives conveniently substituted as $A_3$ adenosine receptor modulators. Other objectives of the present invention are to provide a procedure for preparing these compounds; pharmaceutical compositions comprising an effective amount of these compounds; the use of the compounds for manufacturing a medicament for the treatment of pathological conditions or diseases that can improve by antagonizing the adenosine $A_3$ receptor.

State of the Art

The effects of adenosine are mediated through at least four specific membrane receptors that are classified as $A_1$, $A_{2A}$, $A_{2B}$ and $A_3$ receptors and belong to the family of G protein coupled receptors. The $A_1$ and $A_3$ receptors decreases intracellular levels of cyclic adenosine monophosphate (cAMP) by coupling to inhibitory G proteins (Gi) to inhibit the enzyme adenylate cyclase. In contrast, the $A_{2A}$ and $A_{2B}$ receptors stimulatory G proteins (Gs) to activate adenylate cyclase and increase intracellular cAMP levels are coupled. Through these receptors, adenosine regulates a wide range of physiological functions.

Adenosine $A_3$ Receptors in Gastrointestinal Disorders

Ulcerative colitis and Crohn's disease, collectively known as inflammatory bowel disease, are severe and debilitating disorders with a growing incidence in both developing and advanced countries. (Hanauer, S. B.; Present, D. H. *The state of the art in the management of inflammatory bowel disease*. Rev. Gastroenterol. Disord. 2003, 3, 81-92).

Both diseases are characterized by serious inflammation of the enteric mucosa at different levels of the gastrointestinal tract associated with significant alterations of gastrointestinal motor, secretory, and sensory functions. (De Schepper, H. U.; De Man, J. G.; Moreels, T. G.; Pelckmans, P. A.; De Winter, B. Y. *Review article: gastrointestinal sensory and motor disturbances in inflammatory bowel disease: clinical relevance and pathophysiological mechanisms*. Aliment. Pharmacol. Ther. 2008, 27, 621-637).

Modulators of adenosine $A_3$ receptors are being studied as emerging treatments of bowel inflammation.

Recently it has been confirmed that adenosine $A_3$ ($A_3ARs$) receptors are up-regulated in various autoimmune diseases such as Crohn's disease, rheumatoid arthritis and psoriasis if compared with healthy subjects, whereby said receptor has been considered an important target to treat such autoimmune inflammatory diseases. (Ochaion, A et al. *The anti-inflammatory target A(3) adenosine receptor is over-expressed in rheumatoid arthritis, psoriasis and Crohn's disease*. Cell Immunol. 2009; 258(2):115-22. doi: 10.1016/j.cellimm.2009.03.020. Epub 2009 May 7).

The known $A_3AR$ agonist, IB-MECA, was used in mice to ameliorate intestinal inflammation and spontaneous colitis. In addition, $A_3AR$ stimulation was able to markedly reduce colonic levels of proinflammatory cytokines such as IL-1, IL-6 and IL-12. (Mabley, J.; Soriano, F.; Pacher, P.; Hasko, G.; Marton, A.; Wallace, R.; Salzman, A.; Szabo, C. *The adenosine $A_3$ receptor agonist, N6-(3-iodobenzyl)-adenosine-5'-N-methyluronamide, is protective in two murine models of colitis*. Eur. J. Pharmacol. 2003, 466, 323-329).

Furthermore, a recent study has demonstrated the role of $A_3AR$ in colonic motility and progression of colitis in mouse model induced disease—with dextran sulphate sodium (DSS)-, showing $A_3AR$ knockout mouse model ($A_3$–/–AR) develops fewer symptoms or recover faster than that have the receptor (wild type). The data obtained suggest that activation of $A_3AR$ by endogenous adenosine slows-down intestinal transit, colonic emptying and mass movement (evacuation reflex) and promote stool retention; that disruption of the $A_3AR$ has two important consequences, to alter intestinal motility and protect against DSS-colitis. Therefore, $A_3AR$ is involved in these actions. (Tianhua Ren, MD, PhD et al. *Impact of Disrupting Adenosine $A_3$ Receptors ($A_3$–/–AR) on Colonic Motility or Progression of Colitis in the Mouse*. Inflamm Bowel Dis. 2011, August; 17(8): 1698-1713. doi:10.1002/ibd.21553).

Other studies have shown that in a dextran sodium sulphate-induced colitis model, $A_3R$-deficient mice exhibited reduced colon pathology and decreased tissue myeloperoxidase level, consistent with reduced neutrophil recruitment. However, $A_3R$-deficient mice were unable to resolve the dextran sodium sulphate-induced inflammation and had elevated numbers of tissue-associated bacteria. The data indicate that $A_3ARs$ play a role in neutrophil migration and disrupting this function has the potential to adversely affect innate immune responses. (Butler, M et al. *Impairment of adenosine $A_3$ receptor activity disrupts neutrophil migratory capacity and impacts innate immune function in vivo*. European Journal of Immunology. Sep. 26, 2012, doi: 10.1002/eji.201242655).

Adenosine $A_3$ Receptors in the Central Nervous System $A_3ARs$ are widely distributed in the central nervous system but at low levels and with a reduced affinity. The role of $A_3ARs$ in several pathophysiological conditions is often controversial even if they may contribute to neurotransmission. (Boison, D. *Adenosine as a modulator of brain activity*. Drug News Perspect. 2007, 20, 607-611; Burnstock, G.; Fredholm, B. B.; Verkhratsky, A. *Adenosine and ATP receptors in the brain*. Curr. Top. Med. Chem. 2011, 11, 973-1011).

It has been reported that $A_3AR$ agonists have depressant effects on locomotor activity, suggesting a possible inhibition of excitatory neurotransmission in cortical neurons. (Boison, D. Adenosine as a modulator of brain activity. Drug News Perspect. 2007, 20, 607-611).

Furthermore, a nociceptive role for $A_3ARs$ involving both central nervous system and proinflammatory effects in peripheral tissues has been highlighted. (Yoon, M. H.; Bae, H. B.; Choi, J. I.; Kim, S. J.; Chung, S. T.; Kim, C. M. Roles of adenosine receptor subtypes in the antinociceptive effect of intrathecal adenosine in a rat formalin test. Pharmacology 2006, 78, 21-26).

Major evidence for $A_3ARs$ in neurodegenerative phenomena emerges from studies performed in vivo and in vitro models of hypoxia/ischemia. It has been hypothesized that $A_3ARs$ play a protective role in the first phase of ischemia by decreasing synaptic transmission. (Pugliese, A. M.; Latini, S.; Corradetti, R.; Pedata, F. Brief, repeated, oxygen-glucose deprivation episodes protect neurotransmission from a longer ischemic episode in the in vitro hippocampus: role of adenosine receptors. Br. J. Pharmacol. 2003, 140, 305-314).

Finally, an up-regulation of $A_3ARs$ in the hippocampus of a transgenic mouse model of Alzheimer's disease has been reported, where an altered oxidative phosphorylation was detected prior to amyloid deposition. (von Arnim, C. A.; Spoelgen, R.; Peltan, I. D.; Deng, M.; Courchesne, S.; Koker, M.; Matsui, T.; Kowa, H.; Lichtenthaler, S. F.; Irizarry, M. C.; Hyman, B. T. GGA1 acts as a spatial switch altering amyloid precursor protein trafficking and processing. J. Neurosci. 2006, 26, 9913-9922).

Adenosine $A_3$ Receptors in Renal Disorders

There are published studies showing the harmful effects that can have $A_3AR$ activation in renal ischemia. Particularly, it has been analysed the role of $A_3ARs$ in ischemia induced renal failure in rats by inducing ischemia with micro aneurysm clips after pretreatment with IB-M ECA or an $A_3AR$ antagonist. The data showed that antagonist pretreatment improved blood parameters, like urea and creatinine, and decreased morphological damage in the kidney, and IB-MECA was harmful. (Koscsó, B et al. Investigational $A_3$ adenosine receptor targeting agents. Expert Opin Investig Drugs. 2011 June; 20(6): 757-768. doi:10.1517/13543784.2011.573785 and references therein).

In another study conducted in mouse model of renal ischemia similar results were obtained, checking that renal failure was attenuated both $A_3AR$ receptor deficient mice, as well in mice (wild type) previously treated with an antagonist of said adenosine $A_3$ receptor. (Thomas Lee, H et al. A3 adenosine receptor knockout mice are protected against ischemia- and myoglobinuria-induced renal failure. Am J Physiol Renal Physiol. 2003. 284: F267-F273).

Adenosine $A_3$ Receptors in Cardiovascular System

It is also reported that $A_3ARs$ mediate vascular protection and contribute to limitations in infarct size and in post ischemic myocardium by a mechanism that involves PKC, KATP channel activation, phosphorylation of p38MAPKs, and glycogen synthase kinase (GSk-3β). (Maddock, H. L.; Mocanu, M. M.; Yellon, D. M. Adenosine A3 receptor activation protects the myocardium from reperfusion/reoxygenation injury. Am. J. Physiol.: Heart Circ. Physiol. 2002, 283, H1307-H1313).

Atherosclerosis, a multifactorial disease of the large arteries, is the major cause of heart disease and stroke worldwide. Epidemiological studies have discovered several relevant environmental and genetic risk factors associated with this pathology. Most recently, it has been shown that adenosine through the activation of $A_3ARs$ stimulates VEGF secretion. Adenosine stimulates foam cell formation, and this effect is strongly reduced by $A_3AR$ antagonists.

So, as a consequence, the potential use of $A_3AR$ antagonists could be of interest to block important steps in the atherosclerotic plaque development. (Gessi, S.; Fogli, E.; Sacchetto, V.; Merighi, S.; Varani, K.; Preti, D.; Leung, E.; Maclennan, S.; Borea, P. A. Adenosine modulates HIF-1{alpha}, VEGF, IL-8, and foam cell formation in a human model of hypoxic foam cells. *Arterioscler., Thromb., Vasc. Biol.* 2010, 30, 90-97).

Adenosine $A_3$ Receptors in Immune System $A_3ARs$ are present in immune cells and are involved in the pathophysiological regulation of inflammatory and immune processes. Several results from in vitro and in vivo studies suggest that the activation of $A_3ARs$ can be both pro- or anti-inflammatory depending on the cell type examined or on the animal species considered.

Functional studies have shown that human neutrophils expressed $A_3ARs$, mediating the inhibition of oxidative burst. (van der Hoeven, D.; Wan, T. C.; Auchampach, J. A. Activation of the A3 adenosine receptor suppresses superoxide production and chemotaxis of mouse bone marrow neutrophils. Mol. Pharmacol. 2008, 74, 685-696).

Adenosine $A_3$ Receptors in Respiratory Tract

The role of adenosine in regulating the respiratory system is well-known, and elevated levels of adenosine have been found in bronchoalveolar lavage (BAL), blood and exhaled breath condensate of patients with asthma, and chronic obstructive pulmonary disease (COPD).

$A_3ARs$ have been implicated in inflammatory processes, playing an important role in both pro- or anti-inflammatory responses, strictly depending on different cell type involved. (Salvatore, C. A.; Tilley, S. L.; Latour, A. M.; Fletcher, D. S.; Koller, B. H.; Jacobson, M. A. Disruption of the A3 adenosine receptor gene in mice and its effect on stimulated inflammatory cells. J. Biol. Chem. 2000, 275, 4429-4434).

In particular, the strongest evidence of an $A_3AR$ functional role in mast cell activation comes from the use of genetic knockout mice where the mast cell degranulation in the absence or in the presence of allergen appears to be dependent on adenosine receptor activation. (Zhong, H.; Shlykov, S. G.; Molina, J. G.; Sanborn, B. M.; Jacobson, M. A.; Tilley, S. L.; Blackburn, M. R. Activation of murine lung mast cells by the adenosine A3 receptor. J. Immunol. 2003, 171, 338-345).

The airway hyperresponsiveness is diminished in $A_3AR$ deficient mice, therefore mice treated with selective $A_3AR$ antagonists showed a marked attenuation of pulmonary inflammation, reduced eosinophil infiltration into the airways, and decreased airway mucus production. (Young, H. W.; Molina, J. G.; Dimina, D.; Zhong, H.; Jacobson, M.; Chan, L. N.; Chan, T. S.; Lee, J. J.; Blackburn, M. R. $A_3$ adenosine receptor signaling contributes to airway inflammation and mucus production in adenosine deaminase-deficient mice. J. Immunol. 2004, 173, 1380-1389).

These data suggest the potential use of antagonists of adenosine $A_3$ receptor in conditions related to lung diseases in which inflammation is an important feature.

Adenosine $A_3$ Receptors in Rheumatoid Arthritis

Clinical evidence in rheumatoid arthritis (RA) patients shows that treatment with an adenosine $A_3$ receptor agonist leads to an improvement in signs and symptoms of disease. (Silverman, M. H.; Strand, V.; Markovits, D.; Nahir, M.; Reitblat, T.; Molad, Y.; Rosner, I.; et al, Clinical evidence for utilization of the A3 adenosine receptor as a target to treat rheumatoid arthritis: data from a phase II clinical trial. J. Rheumatol. 2008, 35, 41-48).

The overexpression of $A_3ARs$ in RA has been directly correlated to high levels of proinflammatory cytokines, acting via an upregulation of NF-kB, which is a key player in the pathogenesis of arthritic diseases. (Bar-Yehuda, S.; Silverman, M. H.; Kerns, W. D.; Ochaion, A.; Cohen, S.; Fishman, P. The anti-inflammatory effect of $A_3$ adenosine receptor agonists: a novel targeted therapy for rheumatoid arthritis. Expert Opin. Invest. Drugs 2007, 16, 1601-4613).

In a phase II clinical study in RA patients, IB-MECA oral administration twice daily for 12 weeks was shown to be safe, well tolerated and able to mediate an improvement of disease signs and symptoms, suggesting the development of $A_3$ adenosine receptor modulators as antirheumatic agents.

(Silverman, M. H.; Strand, V.; Markovits, D.; Nahir, M.; Reitblat, T.; Molad, Y.; Rosner, I.; Rozenbaum, M.; Mader, R.; Adawi, M.; et al. Clinical evidence for utilization of the A3 adenosine receptor as a target to treat rheumatoid arthritis: data from a phase II clinical trial. J. Rheumatol. 2008, 35, 41-48).

Adenosine $A_3$ Receptors in Eye Disease

Modulating adenosine $A_3$ receptors as potential therapeutic target for the treatment of various eye diseases such as dry eye syndrome, glaucoma or uveitis has been reported (Y. Zhong, et al., Adenosine, adenosine receptors and glaucoma: An updated overview, Biochim. Biophys. Acta, 2013).

Early studies demonstrated that deletion of adenosine $A_3$ receptors in mice showed a reduction of intraocular pressure, suggesting that $A_3AR$ antagonists may represent a new therapy for glaucoma. (Yang, H.; Avila, M. Y.; Peterson-Yantorno, K.; Coca-Prados, M.; Stone, R. A.; Jacobson, K. A.; Civan, M. M. The cross-species adenosine-receptor antagonist MRS 1292 inhibits adenosine-triggered human nonpigmented ciliary epithelial cell fluid release and reduces mouse intraocular pressure. Curr. Eye Res. 2005, 30, 747-754).

Moreover, $A_3AR$ mRNA and protein have been found to be consistently increased in the nonpigmented ciliary epithelium of the eye in pseudoexfoliation syndrome with glaucoma, compared to normal eye. (Schlotzer-Schrehardt, U.; Zenkel, M.; Decking, U.; Haubs, D.; Kruse, F. E.; Junemann, A.; Coca-Prados, M.; Naumann, G. O. Selective upregulation of the A3 adenosine receptor in eyes with pseudoexfoliation syndrome and glaucoma. *Invest. Ophthalmol. Visual Sci.* 2005, 46, 2023-2034).

$A_3AR$ overexpression in retinal ganglion cells has also been reported. (Zhang, M.; Hu, H. L.; Zhang, X. L.; Lu, W. N.; Lim, J.; Eysteinsson, T.; Jacobson, K. A.; Laties, A. M.; Mitchell, C. H. The A3 adenosine receptor attenuates the calcium rise triggered by NMDA receptors in retinal ganglion cells. Neurochem. Int. 2010, 56, 35-41).

The anti-inflammatory and protective effects mediated via $A_3AR$ prompted to examine the effect of IB-MECA in a model of experimental autoimmune uveitis that represents human uveitis with an autoimmune etiology. In this model, IB-MECA inhibited the clinical and pathological manifestations of uveitis. (Bar-Yehuda, S.; Luger, D.; Ochaion, A.; Cohen, S.; Patokaa, R.; Zozulya, G.; Silver, P. B.; De Morales, J. M. G. R.; Caspi, R. R.; Fishman, P. *Inhibition of experimental auto-immune uveitis by the A3 adenosine receptor agonist CF101*. Int. J. Mol. Med. 2011, 28, 727-731).

Adenosine $A_3$ Receptors in Oncologic Disease $A_3ARs$ are present in different types of tumor cells, such as HL60 and K562 human leukemia, lymphoma, human glioblastoma and in human prostatic cells.

$A_3AR$ are involved in tumor growth and in cell cycle regulation. (Gessi, S.; Merighi, S.; Varani, K.; Cattabriga, E.; Benini, A.; Mirandola, P.; Leung, E.; Mac Lennan, S.; Feo, C.; Baraldi, S.; Borea, P. A. Adenosine receptors in colon carcinoma tissues and colon tumoral cell lines: focus on the A3 adenosine subtype. J. Cell. Physiol. 2007, 211, 826-836).

In particular, the activation of the $A_3ARs$ in prostate cancer cells reducing PKA-mediated stimulation of ERK1/2, and leading to reduce cancer has been reported. (Jajoo, S.; Mukherjea, D.; Watabe, K.; Ramkumar, V. Adenosine A3 receptor suppresses prostate cancer metastasis by inhibiting NADPH oxidase activity. Neoplasia 2009, 11, 1132-1145).

These data suggest that $A_3ARs$ could represent a biological marker and that $A_3AR$ modulation could be used in cancer treatment.

In patent literature are also described different applications related to modulators of adenosine $A_3$ receptor. For example, US 200320387 discloses derivatives of 2,4 disubstituted thiazole having inhibitory properties on the production of pro-inflammatory cytokines and inhibition of said adenosine $A_3$ receptor.

Patent application WO 9921555 discloses compounds 1,3-azole derivatives as antagonists of adenosine $A_3$ receptor and its use as a prophylactic or therapeutic agent for treating asthma, allergies and inflammation, among others.

The document WO 9964418 discloses pyridyl aryl-thiazole as inhibitors of the adenosine $A_3$ receptor and its use as anti-inflammatory agents.

Patent application US 2012134945 discloses the use of antagonists of adenosine $A_3$ receptor in modulate production, secretion and/or accumulation of melanin, as well as methods of treating conditions such as skin hyperpigmentation.

Patent application US 2011190324 discloses the use of antagonists of adenosine $A_3$ receptor for the treatment of atherosclerosis and the combination of such antagonists with other anti-atherosclerotic agents.

Patent application US 2011171130 discloses the use of adenosine $A_3$ receptor antagonists and/or partial agonists for the treatment of numerous diseases, including cancer, inflammatory diseases, asthma, and glaucoma, among others.

Moreover, regarding the treatment of glaucoma and reduction of intraocular pressure in general, several patent documents disclosing different types of antagonists of the adenosine $A_3$ receptor, for example in WO 0003741, WO 2008045330 and US 2012053176.

Other patent documents contained in the prior art, such as WO2009052310, WO2008006369, EP1180518, ES2360632 and ES2204262 disclose the use of different types of adenosine $A_3$ receptor antagonists for the treatment of conditions such as neurological and cardiac ischemia, leukopenia, neutropenia, rheumatoid arthritis, multiple sclerosis, gastrointestinal disorders, respiratory disorders such as asthma and nervous system diseases, such as Alzheimer's disease, Huntington's disease and Parkinson's disease, among others.

Particularly in patent application WO 2005009969, it is mentioned that many antagonists of adenosine $A_3$ receptor disclosed in the literature belong to groups of flavonoids, 1,4-dihydropyridine derivatives, triazoloquinazolines, thyazolopyrimidines thyazolonaphthyridines and having a strong lipophilicity, making them poorly soluble in water. This feature hinders the in vivo applicability of such compounds. Therefore, compounds modulators of adenosine A3 receptor soluble in water are desirable.

Finally, the patent document ES2366075, belonging to present applicant, discloses 2-amino thiazole as potent and selective antagonists of adenosine $A_1$ receptor. The compounds disclosed in said patent document have the following general formula:

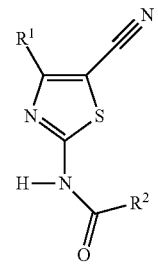

Wherein $R^2$ is selected from an alkyl, cycloalkyl, cycloalkylalkyl and alkylcycloalkyl groups. Said compounds are potent and selective antagonists of adenosine $A_1$ receptor having very low affinity for others adenosine receptors, including the $A_3$ receptors, as shown in the following table.

| Examples ES2366075 | $A_1$ Ki (nM) | $A_3$ Ki (nM) |
|---|---|---|
| 2 | 43 | 2164 |
| 8 | 17 | 1451 |
| 10 | 7 | 7989 |
| 50 | 16 | 1091 |
| 77 | 6 | 1244 |

The present inventors have found that introduction of an aryl or heteroaryl group in position $R^2$ of the general formula above, makes compounds potent modulators of adenosine $A_3$ receptors. Current application discloses new carboxylic acids derivatives of 2-amido 1,3-thiazol as potent modulators of the adenosine $A_3$ receptors.

SUMMARY OF THE INVENTION

In one of its aspects, the present invention refers to 2-amido 1,3-thiazol derivatives of formula (I):

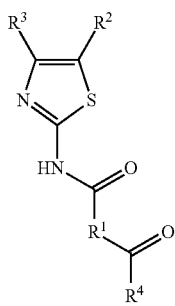

Wherein:
$R^1$ represents a five or six membered aryl or heteroaryl group optionally substituted by one or more substituents selected from the group consisting of halogen atom, $C_1$-$C_6$ alkyl linear or branched, $C_3$-$C_{12}$ cycloalkyl, hydroxyl, $C_1$-$C_6$ alkoxy linear or branched and cyano group,
$R^2$ is selected from the group consisting of halogen atom and cyano group,
$R^3$ represents a five or six membered aryl or heteroaryl group optionally substituted by one or more substituents selected from the group consisting of halogen atom, cyano group, $C_3$-$C_{12}$ cycloalkyl, hydroxyl, $C_1$-$C_6$ alkoxy linear or branched, optionally substituted by one, two or three halogen atoms, $C_1$-$C_6$ alkylthio, amino, mono or dialkylamino, $C_1$-$C_6$ alcoxyalkyl, hydroxycarbonyl and $C_2$-$C_6$ alcoxycarbonyl, and
$R^4$ represents independently:
  a) a hydroxyl group,
  b) —$N(R^5)(R^6)$ group, wherein:
    i) $R^5$ and $R^6$ represent independently a $C_3$-$C_{12}$ cycloalkyl group or $C_1$-$C_4$ alkyl linear or branched, substituted by a carboxyl group (—COOH); or
    ii) $R^5$ and $R^6$ form together with the nitrogen atom to which they are bound a five or six membered saturated cycle comprising optionally a heteroatom selected from N and O, which is substituted by a carboxylic group (—COOH).

Others aspects of the present invention are: a) pharmaceutically acceptable salts thereof, b) pharmaceutical composition comprising an effective amount of said compounds or its pharmaceutically acceptable salts, c) the use of said compounds in the manufacture of a medicament for treating diseases that can be ameliorated by modulation of adenosine $A_3$ receptor, as neurologic disease, such as Alzheimer disease, Huntington disease and Parkinson disease, cardiovascular disease such as atherosclerosis, respiratory diseases such as asthma, oncologic disease such as prostate cancer, kidney diseases such as acute renal failure, autoimmune diseases such as rheumatoid arthritis or diseases of the gastrointestinal system such as Crohn's disease, colitis or irritable bowel syndrome or disease or pathological eye conditions such as glaucoma, dry eye syndrome or uveitis, d) procedures for the treatment a disease that can be ameliorated by modulation of adenosine $A_3$ receptor, as neurologic disease, such as Alzheimer disease, Huntington disease and Parkinson disease, cardiovascular disease such as atherosclerosis, respiratory diseases such as asthma, oncologic disease such as prostate cancer, kidney diseases such as acute renal failure, autoimmune diseases such as rheumatoid arthritis or diseases of the gastrointestinal system such as Crohn's disease, colitis or irritable bowel syndrome or disease or pathological eye conditions such as glaucoma, dry eye syndrome or uveitis, comprising said procedures the administration of compounds of the present invention to a subject in need of treatment, and e) combination comprising a compound of formula (I) according to the invention and other therapeutic agent, wherein said therapeutic agent is selected from agents for treating neurologic disorders such as Alzheimer disease, Huntington disease and Parkinson disease, cardiovascular disease such as atherosclerosis, respiratory diseases such as asthma, oncologic disease such as prostate cancer, kidney diseases such as acute renal failure, autoimmune diseases such as rheumatoid arthritis, diseases of the gastrointestinal system such as Crohn's disease, colitis or irritable bowel syndrome or disease or pathological eye conditions such as glaucoma, dry eye syndrome or uveitis.

As used herein, the term $C_1$-$C_6$ alkyl group is used to design ($C_nH_{2n+1}$) hydrocarbons radicals, linear or branched, optionally substituted, having 1 to 6 carbon atoms. In an embodiment of present invention alkyl groups contain preferably 1 to 4 carbon atoms.

The examples included the following radicals: methyl, ethyl, n-propyl, n-butyl, sec-butyl and terc-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl and iso-hexyl.

As used herein, the term $C_1$-$C_6$ alkoxy group is used to design radicals containing $C_1$-$C_6$ alkyl group linked to an oxygen atom ($C_2H_{2n+1}$—O—), linear or branched, optionally substituted, having 1 to 6 carbon atoms. In an embodiment of present invention alkoxy groups contain preferably 1 to 4 carbon atoms.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term alkylthio group includes radicals containing S and $C_1$-$C_6$ alkyl group, optionally substituted, linear or branched, having 1 to 6 carbon atoms. In an embodiment of present invention alkyl groups contain preferably 1 to 4 carbon atoms.

Preferred alkylthio radicals include methylthio, ethylthio, i-propylthio, n-butylthio, sec-butylthio and terc-butylthio, trifluoromethylthio, difluoromethylthio, hydroximethylthio, 2-hydroxiethylthio or 2-hydroxipropylthio.

As used herein, the term $C_2$-$C_6$ alkoxyalkyl group includes radicals containing an alkyl chain interrupted by at least one oxygen atom. The number of carbon atoms indicates the total number of carbon atoms present in the radical. All structural isomers are included.

As used herein, the term carbonyl means C=O.

As used herein, the term alcoxycarbonyl group is used to design radicals containing $C_2$-$C_6$ alcoxy group, as has been defined previously, and a carbonyl group.

As used herein, the term $C_3$-$C_{12}$ cycloalkyl group is used to design hydrocarbons saturated cycles ($C_nH_{2n-1}$), optionally substituted, and containing 3 to 12 carbons atoms. In an embodiment of present invention alkyl groups contain preferably 3 to 8 carbon atoms.

Preferred cycloalkyl groups, optionally substituted, include cyclopropyl, cyclobutyl, cyclopentyl, cyclohexyl and cycloheptyl. When a cycloalkyl group has two or more substituents, they may be the same or different.

As used herein, the term aryl group is used to design a $C_5$-$C_6$ aryl radical, optionally substituted, for example, phenyl. When an aryl radical has two or more substituents, they may be the same or different.

As used herein, the term heteroaryl group is used to design a five or six membered ring with a heteroatom selected from O, S and N. The heteroaryl group in the present invention can be optionally substituted. In an embodiment of the present invention, the preferred heteroaryl group are thienyl and pyridyl. When a heteroaryl group has two or more substituents, they may be the same or different.

Other preferred heteroaryl groups, optionally substituted, include pyrazinyl, pyrimidinyl, pyridazinyl, furyl, oxadiazolyl, oxazolyl, imidazolyl, 1,3-thiazolyl, thiadiazolyl and pyrazolyl.

As used herein, the term halogen atom includes chlorine, fluorine, bromine or iodine atoms, typically fluorine, chlorine or bromine atom, more preferably chlorine or fluorine atom. The term halo, when is used as prefix has the same meaning.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4 substituents, whereby the hydrogen atoms bound to the unsubstituted atoms, radicals, chains or cycles are replaced by chemically acceptable atoms, radicals, chains or cycles. When two or more substituents are present, each substituent may be the same or different.

As used herein, the term pharmaceutically acceptable salt encompasses salts with acid or base acceptable pharmaceutically. The pharmaceutically acceptable acids include inorganic acids, for example hydrochloric acid, sulphuric acid, phosphoric acid, diphosphoric acid, hydrobromic acid, hydroiodic acid and nitric acid, and organic acids such as citric, maleic, malic, mandelic, ascorbic, oxalic, succinic, tartaric, acetic, methanesulphonic, ethanesulphonic, benzenesulphonic or p-toluenesulphonic. Pharmaceutically acceptable bases include alkali metal (e.g. sodium or potassium and alkaline earth metals (e.g. calcium or magnesium) hydroxides and organic bases, for example alkylamines, arylalkylamines and heterocyclic amines.

Other preferred salts according to the invention are quaternary ammonium compounds wherein an equivalent of an anion (X—) with the positive charge of the N atom. X— may be an anion of various mineral acids such as chloride, bromide, iodide, sulphate, nitrate, phosphate, or an anion of an organic acid such as acetate, maleate, fumarate, citrate, oxalate, succinate, tartrate, malate, mandelate, trifluoroacetate, methanesulfonate and p-toluenesulfonate. X— is preferably an anion selected from chloride, bromide, iodide, sulfate, nitrate, acetate, maleate, oxalate, succinate or trifluoroacetate. More preferably X— is chloride, bromide, trifluoroacetate or methanesulfonate.

According to one embodiment of the present invention in the compounds of formula (I), $R^3$ represents a phenyl group optionally substituted by 1, 2 or 3 halogen atoms, or by a $C_1$-$C_6$ alcoxy group optionally substituted by 1, 2 or 3 halogen atoms. In a more preferred embodiment $R^3$ represents a phenyl group optionally substituted by 1, 2 or 3 halogen atoms or by a $C_1$-$C_6$ alcoxy group. In a further more preferred embodiment, R' is selected from the group consisting of phenyl group and thienyl group, optionally substituted by halogen atoms. In a more preferred embodiment, $R^1$ is selected from the group consisting of phenyl group and thienyl group, optionally substituted by 1, 2 or 3 halogen atoms.

According to one embodiment of the present invention in the compounds of formula (I), $R^4$ represents a hydroxyl group. In a further more preferred embodiment, $R^1$ is selected from the group consisting of phenyl group and thienyl group, optionally substituted by halogen atoms, particularly 1, 2 or 3 halogen atoms and $R^3$ represents a phenyl group optionally substituted by 1, 2 or 3 halogen atoms or by a $C_1$-$C_6$ alcoxyl group, optionally substituted by halogen atoms, particularly 1, 2 or 3 halogen atoms. In a more preferred embodiment $R^3$ represents a phenyl group optionally substituted by 1, 2 or 3 halogen atoms or by one $C_1$-$C_6$ alcoxyl group.

According to other embodiment of the present invention in the compounds of formula (I), $R^1$ is selected from the group consisting of phenyl and thienyl group, optionally substituted by halogen atoms, particularly by 1, 2 or 3 halogen atoms. In a more preferred embodiment $R^1$ is selected from the group consisting of phenyl and thienyl group optionally substituted by 1, 2 or 3 halogen atoms, $R^4$ represents a hydroxy group and $R^2$ represents a halogen atoms.

According to other embodiment of the present invention in the compounds of formula (I), $R^1$ is selected from the group consisting of phenyl and thienyl group, optionally substituted by halogen atoms, particularly by 1, 2 or 3 halogen atoms, $R^4$ represents a hydroxy group and $R^2$ represents a cyano group.

According to other embodiment of the present invention in the compounds of formula (I), $R^1$ is selected from the group consisting of phenyl and thienyl group, optionally substituted by halogen atoms, particularly by 1, 2 or 3 halogen atoms and $R^4$ is selected from the group consisting of [—N($R^5$)($R^6$)], according to has been defined previously. In a more preferred embodiment, in the compounds of formula (I), $R^1$ is selected from the group consisting of phenyl and thienyl group, optionally substituted by 1, 2 or 3 halogen atoms and $R^4$ is selected from the group consisting of [—N($R^5$)($R^6$)], wherein $R^5$ and $R^6$ form together with the nitrogen atom to that they are attached a five or six membered saturated cycle comprising optionally a heteroatom selected from N or O, and is substituted by a carboxylic group (—COOH).

According to one embodiment of the present invention in the compounds of formula (I), $R^4$ represents a hydroxy group, $R^3$ represents a phenyl group optionally substituted by halogen atoms, particularly by 1, 2 or 3 halogen atoms, or by a $C_1$-$C_6$ alcoxy group, optionally substituted by 1, 2 or 3 halogen atoms and $R^1$ represents a phenyl or thienyl group optionally substituted by 1, 2 or 3 halogen atoms.

According to one embodiment of the present invention in the compounds of formula (I), $R^3$ represents a phenyl group optionally substituted by halogen atoms, or by a $C_1$-$C_6$ alcoxy group optionally substituted by 1, 2 or 3 halogen atoms. In a more preferred embodiment $R^3$ represents a phenyl group optionally substituted by 1, 2 or 3 halogen atoms or by one $C_1$-$C_6$ alcoxy group.

According to one embodiment of the present invention in the compounds of formula (I), $R^1$ is selected from the group consisting of phenyl and thienyl group optionally substituted by halogen atoms. In a more preferred embodiment $R^1$ is selected from the group consisting of phenyl and thienyl group optionally substituted by 1, 2 or 3 halogen atoms.

According to an embodiment of the invention in the compounds of formula (I), $R^4$ is selected from the group consisting of [—N($R^5$)($R^6$)] as has been defined previously.

According to an embodiment of the present invention in the compounds of formula (I), $R^4$ is selected from the group consisting of [—N($R^5$)($R^6$)], wherein $R^5$ and $R^6$ form together the nitrogen atom to that they are attached, a five or six membered saturated cycle comprising optionally a heteroatom selected from the group consisting of oxygen and nitrogen, and it is substituted by a carboxilic group (—COOH).

According to a preferred embodiment of the present invention in the compounds of formula (I), $R^1$ represents a phenyl group optionally substituted by 1, 2 or 3 halogen atoms, $R^2$ is selected from the group consisting of cyano group and halogen atom, $R^3$ represents a phenyl group optionally substituted by 1, 2 or 3 halogen atoms or by a $C_1$-$C_6$ alcoxy group optionally substituted by 1, 2 or 3 halogen atoms and $R^4$ represents a hydroxy group, more preferably $R^3$ represents a phenyl group optionally substituted by a methoxy group.

According to a preferred embodiment of the present invention in the compounds of (I), $R^1$ represents a thienyl group optionally substituted by 1, 2 or 3 halogen atoms, $R^2$ is selected from the group consisting of cyano group and halogen atom, $R^3$ represents a phenyl group optionally substituted by 1, 2 or 3 halogen atoms or by $C_1$-$C_6$ alcoxy group optionally substituted by 1, 2 or 3 halogen atoms and $R^4$ represents a hydroxy group; more preferably $R^3$ represents a phenyl group substituted by a methoxy group.

Particular compounds of the invention include:
3-[5-cyano-4-(3,4-dimethoxyphenyl)thiazol-2-ylcarbamoyl]benzoic acid
4-[5-cyano-4-(4-methoxyphenyl)thiazol-2-ylcarbamoyl]benzoic acid
4-(5-cyano-4-phenylthiazol-2-ylcarbamoyl)benzoic acid
3-(5-cyano-4-phenylthiazol-2-ylcarbamoyl)benzoic acid
6-(5-cyano-4-phenylthiazol-2-ylcarbamoyl)pyridine-2-carboxylic acid
3-(5-cyano-4-(4-methoxyphenyl)thiazol-2-ylcarbamoyl)benzoic acid
2-[5-cyano-4-(4-methoxyphenyl)thiazol-2-ylcarbamoyl]benzoic acid
5-(5-cyano-4-(4-methoxyphenyl)thiazol-2-ylcarbamoyl)thiophene-2-carboxylic acid
6-[5-cyano-4-(4-methoxyphenyl)thiazol-2-ylcarbamoyl]pyridine-2-carboxylic acid
3-{5-cyano-4-[4-(trifluoromethoxy)phenyl]thiazol-2-ylcarbamoyl}benzoic acid
5-{5-cyano-4-[4-(trifluoromethoxy)phenyl]thiazol-2-ylcarbamoyl}thiophene-2-carboxylic acid
3-[5-cyano-4-(4-fluorophenyl)thiazol-2-ylcarbamoyl]benzoic acid
5-(5-cyano-4-(4-fluorophenyl)thiazol-2-ylcarbamoyl)thiophene-2-carboxylic acid
5-[5-cyano-4-(3-fluorophenyl)thiazol-2-ylcarbamoyl]thiophene-2-carboxylic acid
5-(5-cyano-4-(2-fluorophenyl)thiazol-2-ylcarbamoyl)thiophene-2-carboxylic acid
3-[5-cyano-4-(pyridin-4-yl)thiazol-2-ylcarbamoyl]benzoic acid
3-[5-cyano-4-(pyridin-2-yl)thiazol-2-ylcarbamoyl]benzoic acid
3-[5-cyano-4-(6-methylpyridin-2-yl)thiazol-2-ylcarbamoyl]benzoic acid
5-(5-cyano-4-(pyridin-3-yl)thiazol-2-ylcarbamoyl)thiophene-2-carboxylic acid
5-(5-cyano-4-(3-cyanophenyl)thiazol-2-ylcarbamoyl)thiophene-2-carboxylic acid
5-(5-cyano-4-(4-cyanophenyl)thiazol-2-ylcarbamoyl)thiophene-2-carboxylic acid
5-(5-cyano-4-phenylthiazol-2-ylcarbamoyl)thiophene-2-carboxylic acid
5-(5-cyano-4-(6-methoxypyridin-3-yl)thiazol-2-ylcarbamoyl)thiophene-2-carboxylic acid
5-((5-cyano-4-(furan-2-yl)thiazol-2-yl)carbamoyl)thiophene-2-carboxylic acid
5-((5-cyano-4-(thiophen-2-yl)thiazol-2-yl)carbamoyl)thiophene-2-carboxylic acid
5-((4-(4-chlorothiophen-2-yl)-5-cyanothiazol-2-yl)carbamoyl)thiophene-2-carboxylic acid
5-((5'-cyano-[2,4'-bithiazol]-2'-yl)carbamoyl)thiophene-2-carboxylic acid
3-((5'-cyano-[2,4'-bithiazol]-2'-yl)carbamoyl)benzoic acid
4-((5'-cyano[2,4'-bithiazol]-2'-yl)carbamoyl)benzoic acid
4-((5-cyano-4-(thiophen-2-yl)thiazol-2-yl)carbamoyl)benzoic acid
3-((5-cyano-4-(thiophen-2-yl)thiazol-2-yl)carbamoyl)benzoic acid
3-((5-cyano-4-(furan-2-yl)thiazol-2-yl)carbamoyl)benzoic acid
4-((5-cyano-4-(furan-2-yl)thiazol-2-yl)carbamoyl)benzoic acid
3-((4-(4-chlorothiophen-2-yl)-5-cyanothiazol-2-yl)carbamoyl)benzoic acid
4-((4-(4-chlorothiophen-2-yl)-5-cyanothiazol-2-yl)carbamoyl)benzoic acid
5-((5-cyano-4-(3-methoxyphenyl)thiazol-2-yl)carbamoyl)thiophene-2-carboxylic acid
3-(5-cyano-4-(6-methoxypyridin-3-yl)thiazol-2-ylcarbamoyl)benzoic acid
5-(5-chloro-4-phenylthiazole-2-ylcarbamoyl)thiophene-2-carboxylic acid
3-(5-chloro-4-phenylthiazole-2-ylcarbamoyl)benzoic acid
5-(5-bromo-4-phenylthiazol-2-ylcarbamoyl)thiophene-2-carboxylic acid
5-(5-fluoro-4-phenylthiazol-2-ylcarbamoyl)thiophene-2-carboxylic acid
3-(5-bromo-4-phenylthiazol-2-ylcarbamoyl)benzoic acid
3-(5-fluoro-4-phenylthiazole-2-ylcarbamoyl)benzoic acid 5-(5-chloro-4-(4-methoxyphenyl)thiazol-2-ylcarbamoyl)
thiophene-2-carboxylic acid
5-[5-cyano-4-(4-methoxyphenyl)thiazol-2-ylcarbamoyl]-
1H-pyrazole-3-carboxylic acid
1-(3-{[5-cyano-4-(4-methoxyphenyl)thiazol-2-yl]
carbamoyl}benzoyl)piperidine-4-carboxylic acid
1-{4-[(5-cyano-4-phenyl-thiazol-2-yl)carbamoyl]
benzoyl}piperidine-4-carboxylic acid
1-{3-[(5-cyano-4-phenyl-thiazol-2-yl)carbamoyl]
benzoyl}piperidine-4-carboxylic acid
1-(5-((5-cyano-4-phenylthiazol-2-yl)carbamoyl)thiophene-
2-carbonyl)piperidine-4-carboxylic acid
1-(4-((5-cyano-4-(thiophen-2-yl)thiazol-2-yl)carbamoyl)
benzoyl)piperidine-4-carboxylic acid
1-(5-((5-cyano-4-(thiophen-2-yl)thiazol-2-yl)carbamoyl)
thiophene-2-carbonyl)piperidine-4-carboxylic acid
1-(3-((5-cyano-4-(thiophen-2-yl)thiazol-2-yl)carbamoyl)
benzoyl)piperidine-4-carboxylic acid.

Compounds defined by formula (I) of the present invention can be synthesized by using the procedures described below.

Scheme 1

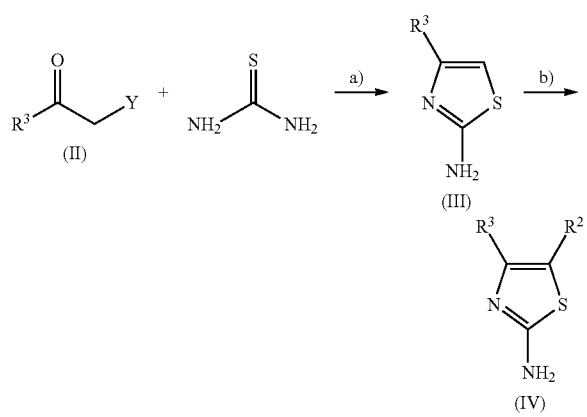

Reagents and conditions: when $R^2$=F, Cl, Br o I. a) Y=halogen, ethanol, 40-100° C. b) $R^2$=F; Selectfluor®, acetonitrile (ACN), 0° C. $R^2$=Cl o Br; N-chlorosuccinimide o N-bromosuccinimide, dimethylformamide (DMF), room temperature/CuX$_2$ (X=Cl, Br o I), acetonitrile; $R^2$=I; iodo chloride (ICl), acetic acid (AcOH)/dichlorometane (DCM), 0° C.

When $R^2$ represents a halogen atom, the corresponding 2-amino-5-halo-1,3-thiazole derivatives of formula (IV) can be obtained by halogenation of derivatives of 2-amino-1,3-thiazole substituted in position 4 of formula (III), which can be commercially available or synthesized as described in Scheme 1.

Fluorination of thiazole ring of compound of formula (III) with bis (chloromethyl)1-chloromethyl-4-fluoro-1,4-diazoniabicyclo[2.2.2] octane (Selectfluor®), gives compounds of formula (IV) with good yields. The fluorination is carried out in acetonitrile at temperatures between 0 and 25° C., to obtain the monofluorinated product (Banks, Eric R., et al J. Chem Soc Perkin 1: 2069-2076). Introducing of remaining halogens it is carried out using the corresponding N-halosuccinimides in DMF at room temperature or with the corresponding salts of copper (II) in acetonitrile (J. Org Chem 2009; 74 (6): 2579-2580). Iodination is executed by the method described by P. Hebeisen (WO2009/068467A1), with iodine monochloride in a mixture of acetic acid and dichloromethane at temperatures between 0 and 25° C.

In the case where derivatives of 2-amino-1,3-thiazole of formula (III) are not commercially available, they can be obtained by the reaction between aryl or heteroarylketones of formula (II), wherein Y is a halogen atom, with thiourea at temperatures between 40° to 100° C., using ethanol or acetonitrile as a solvent, as shown in Scheme 1.

Scheme 2

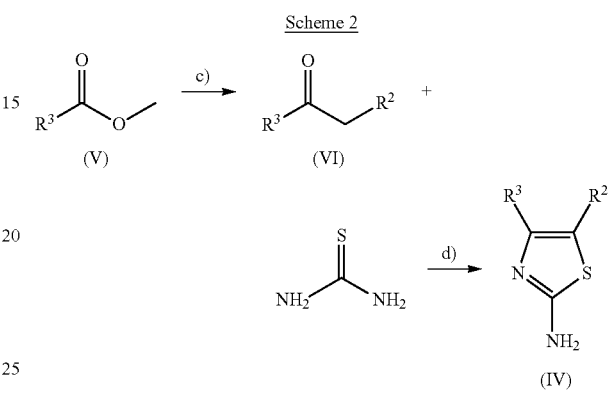

Reagents and conditions: when $R^2$=cyano, c) acetonitrile (ACN), NaH, dimethyl sulfoxide (DMSO), room temperature, d) iodo, pyridine, 40-100° C.

When $R^2$ represents a cyano group, the corresponding derivatives of 2-amino-1,3-thiazol of formula (IV) can be obtained analogously by reaction between commercially available aryl or heteroaryl cyanoketones of formula (VI) with iodine and thiourea, at temperatures between 40° to 100° C., using pyridine as a solvent, as shown in Scheme 2.

In cases where compounds of formula (VI) are not commercially available, those compounds can be synthesized reacting the corresponding esters of formula (V) and acetonitrile in presence of a base like sodium hydride in tetrahydrofuran (THF) or dimethyl sulfoxide (DMSO) as solvent, as shown in Scheme 2.

With this method the following intermediates were synthesized: 3-oxo-3-(pyridin-2-yl)propanenitrile, 3-(6-methylpyridin-2-yl)-3-oxopropanonitrile, 3-oxo-3-(pyridin-3-yl) propanenitrile, 3-(6-metoxipiridin-3-yl)-3-oxopropanonitrile, 4-(2-cyanoacetyl)benzonitrile and 3-(2-cyanoacetyl)benzonitrile, which were used without further purification in the formation of corresponding thiazole, in a reaction style "one-pot" (in one reactor) according to scheme 2.

Scheme 3

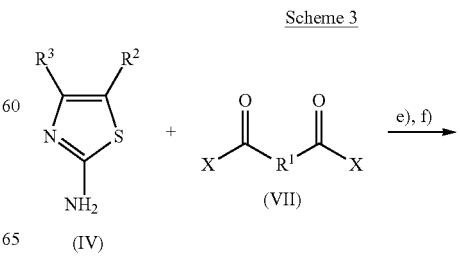

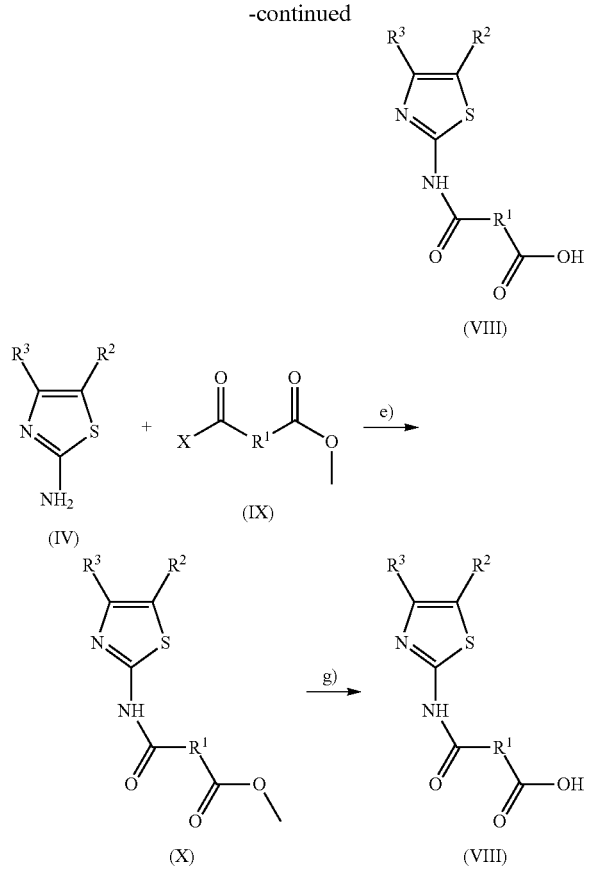

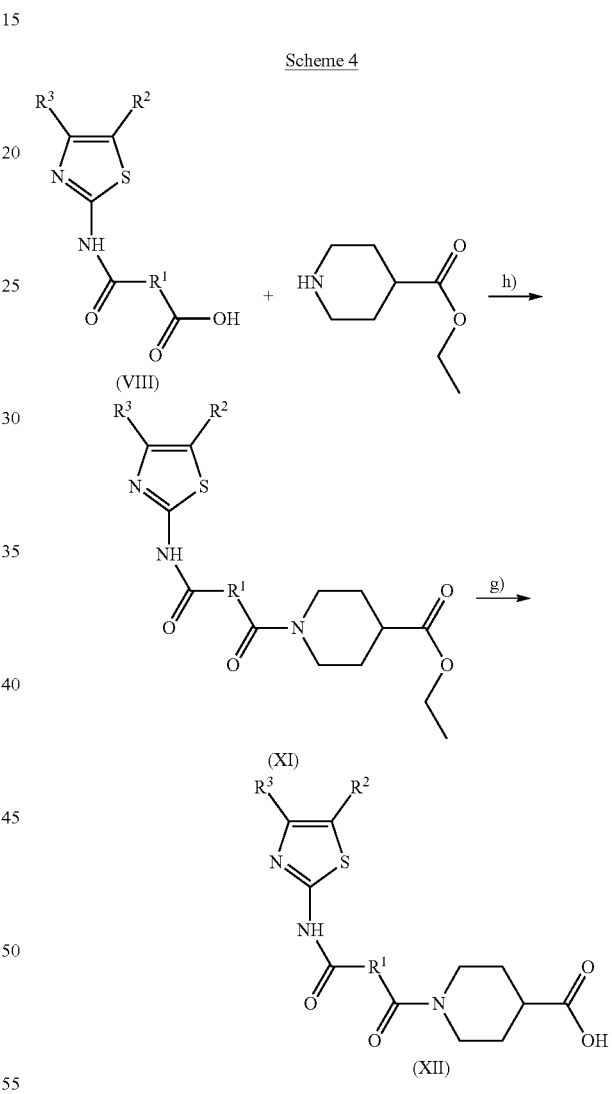

Reagents and conditions: e) when X=Cl, triethylamine (TEA), dimethylaminopyridine (DMAP), acetonitrile (ACN), room temperature; when X=OH, 1H-1,2,3-triazolo[4,5-b]pyridinium, 1-[bis(dimethylamino)methylene]-, 3-oxide, hexafluorophosphate (HATU), ethyldiisopropylamine (DIPEA), dimethylformamide (DMF) 125° C.; f) first dissolve with NaOH, then precipitates with HCl; g) 1M NaOH, THF/$H_2O$, room temperature, then precipitates with HCl.

The derivatives 2-amino thiazole of general formula (IV) can be acylated by reaction of a activated dicarboxylic acid derivatives $XOCR^1OX$ of formula (VII), such as a dicarbonyl dichloride (X=Cl) in the presence of a base like pyridine or triethylamine and dimethylaminopyridine (DMAP) as a catalyzator, in solvents such as dichloromethane (DCM), tetrahydrofuran (THF), DMF, DMSO or ACN at room temperature to yield directly the carboxylic acids of formula (VIII) which are the subject of the present invention and particular cases of the compounds of formula (I).

An alternative procedure consists in the use of ethyl or methyl (chlorocarbonyl)-$R^1$-carboxylate derivatives ($XOCR^1COMe$) (IX) as the acylating agents, with subsequent hydrolysis of the corresponding ethyl or methyl ester (X) obtained, to give again the carboxylic acids of formula (VIII), which are the subject of the present invention.

Moreover, derivatives of formula (IV) can also be acylated using commercially available dicarboxylic acid (X=OH) in presence of an amid coupling reagent as 1H-1,2,3-Triazolo[4,5-b] pyridinium, 1-[bis(dimethylamino)methylene]-, 3-oxide, hexafluorophosphate (HATU), to lead also compounds of formula (VIII), which are particular cases of the compounds of formula (I) according to the invention.

Acid chlorides of formula (VII) required for the synthesis of compounds of formula (VIII) can be synthesized easily from the corresponding dicarboxylic acids using synthesis methods well described in the literature (Burdett, K A, Synthesis, 1991, 441-42).

Acid derivatives of formula (VIII) can be reacted with the corresponding amines or commercial aminoesters such as ethyl or methyl isonipecotate in the presence of HATU to obtain amides or amidoesteres of formula (XI). These compounds can be hydrolyzed with sodium hydroxide resulting carboxylic acids of formula (XII) as shown in Scheme 4, which are particular cases of compounds of formula (I) according to the invention.

Scheme 4

Reagents and conditions: h) HATU, DIPEA, DMF; g) 1M NaOH, THF/$H_2O$, room temperature, then precipitates with HCl.

Pharmacological Activity

Adenosine Receptor Subtypes Competition Radioligand Binding Assay

Human recombinant membranes with adenosine receptors were purchased from Receptor Biology, Inc. (USA).

Competitive assays were carried out by incubation of membranes from human $A_3$ receptors transfected to CHO cells, [$^3$H]-NECA, buffer (20 mM HEPES (pH 7.4), 100 mM NaCl, 10 mM MgCl$_2$, 2 units/ml adenosine deaminase), and unlabelled ligand in a total volume of 0.2 ml for 60 min at 25° C. R-PIA was used to determine nonspecific binding. It was filtered over Schleicher & Schuell GF/52 (presoaked with 0.5% polyethyleneimine) in a Brandel cell harvester. The unbound radioligand was removed with 3×250 µl of 20 mM HEPES (pH 7.4), 100 mM NaCl, 10 mM MgCl$_2$.

In Table 1, binding constants to adenosine A$_3$ receptor obtained for some examples are shown.

TABLE 1

| Examples | COMPOUNDS | Binding to adenosine A$_1$ receptor (Ki nM) | Binding to adenosine A$_3$ receptor (Ki nM) |
|---|---|---|---|
| Example 6 | 3-(5-cyano-4-(4-methoxyphenyl)thiazol-2-ylcarbamoyl)benzoic acid | >1000 | 10 |
| Example 8 | 5-(5-cyano-4-(4-methoxyphenyl)thiazol-2-ylcarbamoyl)thiophene-2-carboxylic acid | >1000 | 23 |
| Example 13 | 5-(5-cyano-4-(4-fluorophenyl)thiazol-2-ylcarbamoyl)thiophene-2-carboxylic acid | 131 | 66 |
| Example 15 | 5-(5-cyano-4-(2-fluorophenyl)thiazol-2-ylcarbamoyl)thiophene-2-carboxylic acid | >500 | 99 |
| Example 22 | 5-(5-cyano-4-phenylthiazol-2-ylcarbamoyl)thiophene-2-carboxylic acid | 87 | 66 |
| Example 25 | 5-((5-cyano-4-(thiophen-2-yl)thiazol-2-yl)carbamoyl)thiophene-2-carboxylic acid | ND | 36 |
| Example 26 | 5-((4-(4-chlorothiophen-2-yl)-5-cyanothiazol-2-yl)carbamoyl)thiophene-2-carboxylic acid | ND | 12 |
| Example 37 | 3-(5-cyano-4-(6-methoxypyridin-3-yl)thiazol-2-ylcarbamoyl)benzoic acid | >1000 | 99 |
| Example 38 | 5-(5-chloro-4-phenylthiazole-2-ylcarbamoyl)thiophene-2-carboxylic acid | 34 | 21 |
| Example 41 | 5-(5-fluoro-4-phenylthiazol-2-ylcarbamoyl)thiophene-2-carboxylic acid | 64 | 10 |
| Example 44 | 5-(5-chloro-4-(4-methoxyphenyl)thiazol-2-ylcarbamoyl)thiophene-2-carboxylic acid | >1000 | 24 |
| Example 46 | 1-{3-[(5-cyano-4-phenylthiazol-2-yl)carbamoyl]benzoyl}piperidine-4-carboxylic acid | 73 | 27 |

ND: Not determined

From the above results it can be concluded that the compounds of formula (I) claimed by the present invention are potent modulators of the adenosine A$_3$ receptor.

Another aspect of the present invention is addressed to the use of a compound of formula (I) according to the present invention for the manufacture of a medicament for treating a pathological condition or disease susceptible to amelioration by modulating A$_3$ receptors adenosine.

The compounds of the present invention are useful in the treatment or prevention of diseases known to be ameliorated by treatment with a modulator of the adenosine A$_3$ receptors. Such diseases are for example: ophthalmologic disease conditions such as glaucoma, dry eye syndrome or uveitis, neurological disorders such as Alzheimer's disease, cardiovascular diseases such as atherosclerosis, respiratory diseases such as asthma, renal diseases such as acute renal failure, oncological diseases such as prostate cancer, autoimmune diseases such as rheumatoid arthritis or diseases of gastrointestinal system such as irritable bowel syndrome.

Accordingly, the compounds of the invention, the pharmaceutical acceptable salts thereof and pharmaceutical compositions comprising said compounds and/or salts thereof, can be used in a method for the treatment of disorders of the human body with comprises administering to a subject in need of such treatment an effective amount of a derivative of 2-amino-1,3-thiazole of formula (I) claimed in the invention or a pharmaceutically acceptable salts thereof.

The current invention also provides pharmaceutical compositions comprising, as active ingredient, at least a 2-amino-1,3-thiazole derivative of formula (I) according to the present invention or a pharmaceutically acceptable salt thereof together with a pharmaceutically acceptable carrier or diluent. The active ingredient may comprise from 0.001% to 99% by weight, preferably from 0.01. % to 90% by weight of the composition, depending on the nature of the formulation and whether further dilution before application is performed. Preferably, the compositions are prepared in a form suitable for oral, topical, nasal, rectal, percutaneous or injectable administration.

The pharmaceutically acceptable excipients which are admixed with the active compound, or salts of such compound, to form compositions of this invention are well known per se and the actual excipients used depend inter alia on the intended method of administering the compositions.

The compositions of this invention are adapted preferably for injectable and per os administration. In this case, the compositions for oral administration may take the form of tablets, prolonged action tablets, sublingual tablets, capsules, inhalation aerosols, inhalation solutions, dry powder inhalation, or liquid preparations, such as mixtures, elixirs, syrups or suspensions, all containing the compound of the invention; such preparations may be prepared by methods known in the art.

The diluents which may be used in the preparation of the compositions include those liquid and solid diluents which are compatible with the active ingredient, together with coloring or flavoring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound together with, for example, sucrose to form a syrup. The suspensions may comprise an insoluble active compound of the invention or a pharmaceutically acceptable salt thereof together with water and with a suspending agent or flavoring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

Another aspect of the invention is addressed to a combination product comprising a compound of formula (I) according to has been defined previously and other drugs accepted to treat diseases of central nervous system as for example Alzheimer's disease, cardiovascular disease as for example atherosclerosis, respiratory diseases as asthma, renal disease as acute renal failure, oncologic diseases as prostate cancer, autoimmune diseases as rheumatoid arthritis or diseases of the gastrointestinal system such as irritable bowel syndrome.

Another aspect of the invention is addressed to a combination product comprising a compound of formula (I) according to has been defined previously, and other drugs, wherein the other drugs are selected from the group consisting of Montelukast, Bicalutamide, Flutamide, Tofacitinib, and a diuretic selected from Hydrochlorothiazide and Lubiprostone for the treatment of disease selected from asthma, prostate cancer, rheumatoid arthritis, acute renal failure and irritable bowel syndrome and glaucoma.

The present invention will be further illustrated by the following examples. The following are given by way of illustration and do not limit the scope of the invention in any way.

EXAMPLES

The synthesis of compounds and intermediates of the invention for use herein are illustrated by the following Examples (1 to 52), including the preparation of the intermediates, which do not limit in any way the scope of the present invention.

General.

Reagents, solvents and starting materials were purchased from commercial suppliers. Concentration refers to evaporation under vacuum using a Büchi rotatory evaporator. Reaction products were purified when necessary, by flash chromatography on silica gel (40-63 μm) with the solvent system indicated. Spectroscopic data were recorded on a Varian Gemeni 300 spectrometer. Melting points were recorded on a Büchi 535 apparatus. HPLC-MS were performed on a Gilson instrument equipped with a Gilson piston pump 321, a Gilson 864 vacuum degasser, a Gilson 189 injection module, a 1/1000 splitter, a Gilson 307 make-up pump, a Gilson 170 diode array detector, and a Thermoquest Fennigan aQa detector.

General Method for the Synthesis of Acid Chlorides

Acid chlorides of formula (VII) are synthesized from the corresponding commercial carboxylic acids using the synthesis method described in the literature. (Burdett, K. A., *Sintesis*, 1991, 441-42).

Intermediate 1:
2-amino-4-(pyridin-2-yl)thiazole-5-carbonitrile

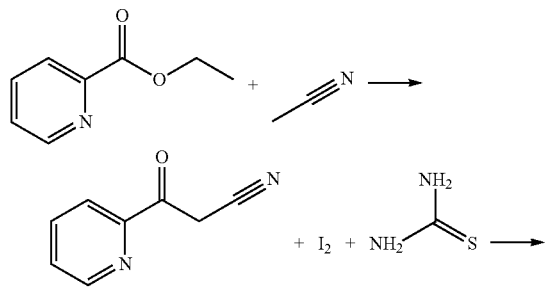

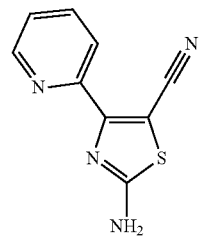

A suspension of sodium hydride in mineral oil (60%) (0.81 g, 16.52 mmol) was added to a solution of 0.95 ml (18.02 mmol) of acetonitrile in 10 ml of THF, and stirred for 15 min. To this suspension, a solution of 2.27 g (15.02 mmol) of ethyl picolinate in 5 ml of THF is dropped slowly. After about 10 min of stirring a white precipitate is formed. The reaction mixture is stirred at room temperature overnight, and then 30 ml of pyridine, 2.28 g (30 mmol) of thiourea and 3.81 g (15 mmol) of iodine were added, and the mixture stirred 90° C. for 6 h. The reaction was then allowed to reach room temperature and poured into cold water. The precipitate formed is filtered, washed several times with cold water and dried. 1.85 g (61%) of a black solid are obtained.

$^1$H-NMR (400 MHz, DMSO-$d_6$): δ=7.46 (m, 1H), 7.93 (m, 2H), 8.21 (s, 2H), 8.66 (d, 1H).

Intermediates 2 to 8 were synthesized using the procedure described for Intermediate 1 using the corresponding esters: 6-methyl-2-pyridinecarboxylate, methyl nicotinate, methyl 2-methoxypyridin-5-carboxylate, methyl 4-cyanobenzoate, methyl 3-cyanobenzoate, methyl 4-chlorothiophene-2-carboxylate, and methyl thiazole-2-carboxylate through intermediates: 3-(6-methylpyridin-2-yl)-3-oxopropanonitrile, 3-oxo-3-(pyridin-3-yl)propanonitrile, 3-(6-methoxy-3-yl)-3-oxopropanonitrile, 4-(2-cyanoacetyl)benzonitrile, 3-(2-cyanoacetyl) benzonitrile, 3-(4-chlorothiophen-2-yl)-3-oxopropanenitrile and 3-oxo-3-(thiazol-2-yl)propanenitrile respectively, to finally obtain the corresponding thiazole.

Intermediate 2: 2-amino-4-(6-methylpyridin-2-yl)thiazole-5-carbonitrile $^1$H-NMR (400 MHz, DMSO-$d_6$): δ=2.51 (s, 3H), 7.31 (d, 1H), 7.71 (d, 1H), 7.81 (t, 1H), 8.17 (d, 2H).

Intermediate 3:
2-amino-4-(pyridin-3-yl)thiazole-5-carbonitrile $^1$H-NMR (400 MHz, DMSO-$d_6$): δ=7.56 (dd, 1H), 8.25 (d, 1H), 8.33 (s, 2H), 8.67 (dd, 1H), 9.07 (d, 1H).
HPLC-MS: Rt 2.249 m/z 203.0 (MH$^+$).

Intermediate 4: 2-amino-4-(6-methoxypyridin-3-yl)thiazole-5-carbonitrile $^1$H-NMR (400 MHz, DMSO-$d_6$): δ=3.91 (s, 3H), 6.97 (d, 1H), 8.17 (dd, 1H), 8.27 (s, 2H), 8.71 (d, 1H).
HPLC-MS: Rt 2.949 m/z 233.0 (MH$^+$).

Intermediate 5:
2-amino-4-(4-cyanophenyl)thiazole-5-carbonitrile $^1$H-NMR (400 MHz, DMSO-$d_6$): δ=7.99 (d, 2H), 8.07 (d, 2H), 8.33 (s, 2H).
HPLC-MS: Rt 3.077 m/z 227.0 (MH$^+$).

Intermediate 6: 2-amino-4-(3-cyanophenyl)thiazole-5-carbonitrile $^1$H-NMR (400 MHz, DMSO-d$_6$): δ=7.76 (t, 1H), 7.97 (d, 1H), 8.23 (m, 2H), 8.34 (s, 2H).
HPLC-MS: Rt 3.169 m/z 227.0 (MH$^+$).

Intermediate 7: 2-amino-4-(4-chlorothiophen-2-yl)thiazole-5-carbonitrile $^1$H-NMR (400 MHz, DMSO-d$_6$): δ=8.36 (s, 2H), 7.79 (d, 1H), 7.63 (d, 1H).
HPLC-MS: Rt 3.639, m/z 241.9 (M$^+$).

Intermediate 8: 2'-amino-[2,4'-bithiazole]-5'-carbonitrile $^1$H-NMR (400 MHz, DMSO-d$_6$): δ=8.39 (5, 2H), 8.04 (d, 1H), 7.94 (d, 1H)
HPLC-MS: Rt 3.639, m/z 241.9 (M$^+$)

Intermediate 9: 2-amino-4-(4-methoxyphenyl)thiazole-5-carbonitrile

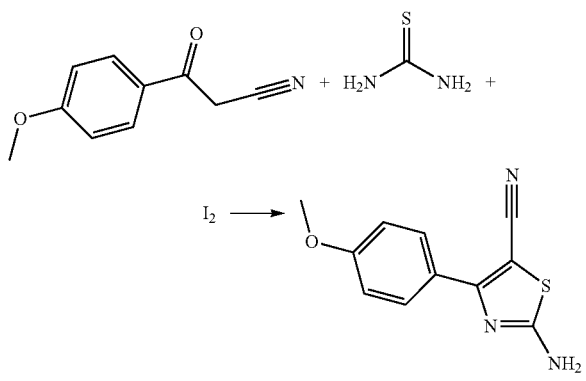

5.07 g (28.94 mmol) of 3-(4-methoxyphenyl)-3-oxopropanonitrile were dissolved in pyridine (30 ml) and 3.08 g (40.5 mmol) of thiourea and 7.35 g (28.94 mmol) of iodine were added. The solution was heated for 6 hours at 90° C. The solution was then cooled to room temperature and poured into ice water (500 ml). The resulting solid was filtered, washed with water several times to obtain 5.11 g (76.35%) of a light brown solid.
$^1$H-NMR (400 MHz, DMSO-d$_6$): δ=3.84 (s, 3H), 7.09 (d, 2H), 8.08 (d, 2H), 8.38 (d, 2H).

The following intermediates have been synthesized using the procedure described for Intermediate 9 using the corresponding oxonitriles.

Intermediate 10: 2-amino-4-(3,4-dimethoxyphenyl)thiazole-5-carbonitrile $^1$H-NMR (400 MHz, DMSO-d$_6$): δ=3.77 (s, 3H), 3.80 (s, 3H), 7.06 (d, 1H), 7.48 (s, 1H), 7.53 (d, 1H), 8.18 (s, 2H).

Intermediate 11: 2-amino-4-phenylthiazole-5-carbonitrile $^1$H-NMR (400 MHz, DMSO-d$_6$): δ=7.47 (t, 1H), 7.55 (t, 2H), 8.09 (d, 2H), 8.39 (d, 2H).

Intermediate 12: 2-amino-4-[4-(trifluoromethoxy)phenyl]thiazole-5-carbonitrile $^1$H-NMR (400 MHz, DMSO-d$_6$): δ=7.54 (d, 2H), 8.02 (d, 2H), 8.29 (s, 2H).

Intermediate 13: 2-amino-4-(4-fluorophenyl)thiazole-5-carbonitrile $^1$H-NMR (400 MHz, DMSO-d$_6$): δ=7.36 (t, 2H), 7.97 (dd, 2H), 8.25 (s, 2H).
HPLC-MS: Rt 3.316 m/z 220.0 (MH$^+$).

Intermediate 14: 2-amino-4-(3-fluorophenyl)thiazole-5-carbonitrile $^1$H-NMR (400 MHz, DMSO-d$_6$): δ=7.34 (td, 1H), 7.60-7.53 (m, 1H), 7.64 (ddd, 1H), 7.80-7.74 (m, 1H), 8.28 (s, 2H).
HPLC-MS: Rt 3.373 m/z 220.0 (MH$^+$).

Intermediate 15: 2-amino-4-(2-fluorophenyl)thiazole-5-carbonitrile $^1$H-NMR (400 MHz, DMSO-d$_6$): δ=7.32 (m, 2H), 7.54 (d, 1H), 7.64 (m, 1H), 8.26 (s, 2H).
HPLC-MS: Rt 2.950 m/z 219.4 (MH$^+$).

Intermediate 16: 2-amino-4-(pyridin-4-yl)thiazole-5-carbonitrile $^1$H-NMR (400 MHz, DMSO-d$_6$): δ=7.83 (d, 2H), 8.35 (s, 2H), 8.74 (d, 2H).

Intermediate 17: 2-amino-4-(3-methoxyphenyl)thiazole-5-carbonitrile $^1$H-NMR (400 MHz, DMSO-d$_6$): δ=3.80 (s, 3H), 7.06 (dd, 1H), 7.42 (d, 1H), 7.45 (dd, 1H), 7.51 (dd, 1H), 8.26 (s, 2H).
HPLC-MS: Rt 3.530, m/z 232.0 (MH$^+$).

Intermediate 18: 2-amino-4-(furan-2-yl)thiazole-5-carbonitrile $^1$H-NMR (400 MHz, DMSO-d$_6$): δ=8.22 (s, 2H), 7.89 (d, 1H), 6.93 (d, 1H), 6.68 (dd, 1H).
HPLC-MS: Rt 2.615, m/z 192.0 (MH$^+$)

Intermediate 19: 2-amino-4-(thiophen-2-yl)thiazole-5-carbonitrile $^1$H-NMR (400 MHz, DMSO-d$_6$): δ=7.21 (dd, 1H), 7.74 (s, 1H), 737-7.80 (m, 1H), 8.31 (s, 2H).
HPLC-MS: Rt 3.141, m/z 208.0 (MH$^+$)

Intermediate 20: 5-fluoro-4-phenylthiazol-2-amine

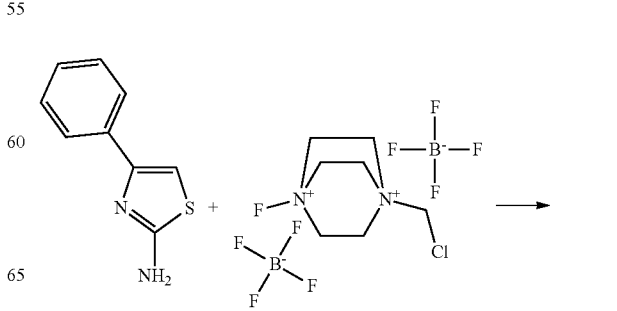

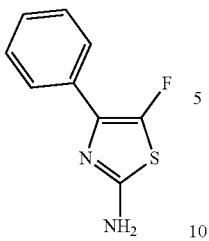

1.1 g (3.12 mmol) of Selectfluor® were dissolved in 4-phenylthiazole-2-amina (0.5 g, 2.83 mmol) in 10 ml of acetonitrile cooled in an ice bath, was stirred for 15 min at this temperature, then cooled to room temperature and stirred for 12 hours. The solvent was removed by rotoevaporation, and the solution was filtered through gel silica using a mixture ethyl acetate/cyclohexane.

$^1$H-NMR (400 MHz, DMSO-$d_6$): δ=6.97 (s, 2H), 7.28 (t, 1H), 7.41 (t, 2H), 7.70 (t, 2H).

HPLC-MS: Rt 3.568 m/z 195.0 (MH$^+$).

Intermediate 21: 5-chloro-4-phenylthiazol-2-amine 0.378 g (2.83 mmol) of N-chlorosuccinimide were added to 0.5 g (2.83 mmol) of 4-phenylthiazol-2-amine in 1.5 ml DMF. The reaction mixture was stirred for 12 h, and then poured into brine. The precipitate formed, filtered, washed several times with cold water and dried to obtain the desired compound.

$^1$H-NMR (400 MHz, DMSO-$d_6$): δ=7.32 (dd, 3H), 7.42 (t, 2H), 7.81 (m, 2H).

HPLC-MS: Rt 3.768 m/z 211.0 (MH$^+$).

The following intermediates were synthesized using the procedure described for Intermediate 21 with N-chloro- or N-bromosuccinimide and the corresponding thiazole.

Intermediate 22:
5-chloro-4-(4-methoxyphenyl)thiazol-2-amine $^1$H-NMR (400 MHz, DMSO-$d_6$): δ=3.78 (s, 3H), 6.98 (d, 2H), 7.22 (s, 2H), 7.77 (d, 2H).

HPLC-MS: Rt 3.776 m/z 241.0 (MH$^+$).

Intermediate 23: 5-bromo-4-phenylthiazol-2-amine $^1$H-NMR (400 MHz, DMSO-$d_6$): δ=7.30 (s, 2H), 7.36 (m, 1H), 7.42 (m, 2H), 7.80 (m, 2H).

HPLC-MS: Rt 3.781 m/z 254.9 (M$^+$).

Intermediate 24:
5-bromo-4-(4-methoxyphenyl)thiazol-2-amine $^1$H-NMR (400 MHz, DMSO-$d_6$): δ=3.78 (s, 3H), 6.98 (d, 2H), 7.29 (s, 2H), 7.76 (d, 2H).

HPLC-MS: Rt 3.78 m/z 286.1 (MH$^+$).

Intermediate 25: Methyl 5-((5-cyano-4-phenylthiazol-2-yl)carbamoyl)thiophene-2-carboxylate

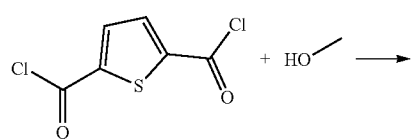 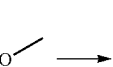

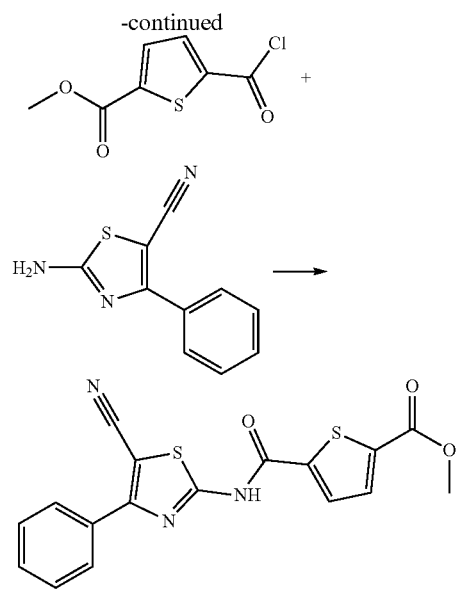

13.5 g (64.6 mmol) of thiophene-2,5-dicarbonyl dichloride were dissolved in dry acetonitrile (ACN) (250 mL) and the solution was cooled in an ice water bath. Then 2.62 ml (64.6 mmol) of dry methanol and 20.8 ml (149.07 mmol) of triethylamine were added. The resulting suspension was allowed to reach room temperature and stirred at this temperature for 1 h. The obtained acylchloride has been used in the next step without further purification.

10 g (49.69 mmol) of 2-amino-4-phenylthiazole-5-carbonitrile, 10 mg of DMAP and additional 20 ml of ACN were added to the above described suspension of the acylchloride. The reaction mixture was stirred 2 h at 40° C. The complete consumption of the starting material was followed by TLC. Triethylamine hydrochloride was removed by filtration and the resulting solution was poured into a cooled NaHCO$_3$ solution (1.5 L). The resulting solid was filtered, washed with water and 2 times additionally with water at 60° C. The brown solid was re-suspended in 500 ml of ACN and poured again into a NaHCO$_3$ solution (1.5 L). The precipitate was filtered, washed with water at room temperature, the washed two times additionally with water at 60° C., and dried. The resulting brown solid was washed shortly with cold diethyl ether to obtain the desired compound $^1$H-NMR (400 MHz, DMSO-$d_6$): δ=3.86 (s, 3H), 7.57 (m, 3H), 7.88 (d, 1H), 8.03 (d, 2H), 8.20 (s, 1H), 13.89 (s, 1H).

The following intermediates were synthesized using the procedure described for Intermediate 25 employing the corresponding ethyl or methyl (chlorocarbonyl)-R$^1$-carboxylate derivatives and 2-amino thiazole.

Intermediate 26: Methyl 5-(5-cyano-4-(6-methoxypyridin-3-yl)thiazol-2-ylcarbamoyl)thiophene-2-carboxylate $^1$H-NMR (400 MHz, DMSO-$d_6$): δ=3.86 (d, 3H), 3.94 (s, 3H), 7.01 (d, 1H), 7.82 (m, 1H), 7.95 (d, 1H), 8.28 (dd, 1H), 8.82 (dd, 1H), 13.84 (s, 1H).

Intermediate 27: Methyl 5-((5-cyano-4-(furan-2-yl)thiazol-2-yl)carbamoyl)thiophene-2-carboxylate $^1$H-NMR (400 MHz, DMSO-$d_6$): δ=3.87 (s, 3H), 6.75 (dd, 1H), 7.09 (dd, 1H), 7.88 (d, 1H), 7.99 (dd, 1H), 8.29 (d, 1H), 13.96 (s, 1H).

Intermediate 28: Methyl 5-((5-cyano-4-(thiophen-2-yl)thiazol-2-yl)carbamoyl)thiophene-2-carboxylate $^1$H-NMR (400 MHz, DMSO-d$_6$): δ=3.87 (s, 3H), 7.28 (dd, 1H), 7.84 (dd, 1H), 7.89-7.93 (m, 2H), 8.32 (d, 1H), 13.94 (s, 1H).

Intermediate 29: Methyl 5-((4-(4-chlorothiophen-2-yl)-5-cyanothiazol-2-yl)carbamoyl)thiophene-2-carboxylate $^1$H-NMR (400 MHz, DMSO-d$_6$): δ=3.87 (s, 3H), 7.73 (s, 1H), 7.89 (s, 2H), 8.30 (s, 1H), 13.97 (s, 1H).

Intermediate 30: Methyl 5-((5'-cyano-[2,4'-bithiazol]-2'-yl)carbamoyl)thiophene-2-carboxylate $^1$H-NMR (400 MHz, DMSO-d$_6$): δ=3.87 (s, 1H), 7.89 (d, 1H), 8.04 (d, 1H), 8.13 (d, 1H), 8.32 (d, 1H), 14.02 (s, 1H).

Intermediate 31: Methyl 3-((5'-cyano-[2,4'-bithiazol]-2'-yl)carbamoyl)benzoate $^1$H-NMR (400 MHz, DMSO-d$_6$): δ=3.92 (s, 3H), 7.74 (t, 1H), 8.04 (d, 1H), 8.13 (d, 1H), 8.23 (d, 1H), 8.40 (d, 1H), 8.75 (s, 1H), 13.94 (s, 1H).

Intermediate 32: Methyl 4-((5'-cyano-[2,4'-bithiazol]-2'-yl)carbamoyl)benzoate $^1$H-NMR (400 MHz, DMSO-d$_6$): δ=3.90 (s, 3H), 8.04 (d, 1H), 8.12 (dd, 3H), 8.26 (d, 2H), 13.89 (s, 1H).
HPLC-MS: Rt 3.263, m/z 371.0 (MH$^+$).

Intermediate 33: Methyl 4-((5-cyano-4-(thiophen-2-yl)thiazol-2-yl)carbamoyl)benzoate $^1$H-NMR (400 MHz, DMSO-d$_6$): δ=3.90 (s, 3H), 7.29 (dd, J=5.0, 3.8 Hz, 1H), 7.86-7.80 (m, 1H), 7.95-7.89 (m, 1H), 8.14-8.08 (m, 2H), 8.25 (d, J=8.5 Hz, 2H), 13.80 (s, 1H).
HPLC-MS: Rt 3.767, m/z 371.0 (MH$^+$)

Intermediate 34: Methyl 3-((5-cyano-4-(thiophen-2-yl)thiazol-2-yl)carbamoyl)benzoate $^1$H-NMR (400 MHz, DMSO-d$_6$): δ=3.92 (s, 3H), 7.28 (dd, 1H), 7.73 (t, 1H), 7.84 (dd, 1H), 7.92 (dd, 1H), 8.20-8.25 (m, 1H), 8.39 (dd, 1H), 8.73 (t, 1H), 13.83 (s, 1H).
HPLC-MS: Rt 3.867, m/z 370.0 (MH$^+$)

Intermediate 35: Methyl 3-((5-cyano-4-(furan-2-yl)thiazol-2-yl)carbamoyl)benzoate $^1$H-NMR (400 MHz, DMSO-d$_6$): δ=3.92 (s, 3H), 6.76 (dd 1H), 7.11 (dd, 1H), 7.74 (t, 1H), 8.00 (dd, 1H), 8.21-8.25 (m, 1H), 8.37-8.42 (m, 1H), 8.73 (t, 1H), 13.87 (s, 1H).
HPLC-MS: Rt 3.515, m/z 354.0 (MH$^+$)

Intermediate 36: Methyl 4-((5-cyano-4-(furan-2-yl)thiazol-2-yl)carbamoyl)benzoate $^1$H-NMR (400 MHz, DMSO-d$_6$): δ=4.00 (s, 3H) 7.24 (m, 1H), 7.65 (m, 1H), 8.11 (d, 2H), 8.17 (d, 1H), 8.26 (d, 2H).
HPLC-MS: Rt 3.435, m/z 354.0 (MH$^+$)

Intermediate 37: Methyl 3-((4-(4-chlorothiophen-2-yl)-5-cyanothiazol-2-yl)carbamoyl)benzoate $^1$H-NMR (400 MHz, DMSO-d$_6$): δ=3.91 (s, 3H), 7.72 (t, 2H), 7.87 (s, 1H), 8.21 (d, 1H), 8.38 (d, 1H), 8.72 (s, 1H), 13.84 (s, 1H).

Intermediate 38: Methyl 4-((4-(4-chlorothiophen-2-yl)-5-cyanothiazol-2-yl)carbamoyl)benzoate $^1$H-NMR (400 MHz, DMSO-d$_6$): δ=3.89 (s, 3H), 7.72 (s, 1H), 7.87 (s, 1H), 8.08 (d, 2H), 8.23 (d, 2H), 13.80 (s, 1H).

Intermediate 39: Methyl 5-((5-cyano-4-(3-methoxyphenyl)thiazol-2-yl)carbamoyl)thiophene-2-carboxylate $^1$H-NMR (400 MHz, DMSO-d$_6$): δ=3.92 (s, 3H), 3.97 (s, 3H), 7.21 (m, 1H), 7.52 (d, 1H), 7.57 (m, 1H), 7.64 (m, 1H), 7.86 (d, 1H), 8.17 (d, 1H).

Intermediate 40: Methyl 3-(5-cyano-4-(6-methoxypyridin-3-yl)thiazol-2-ylcarbamoyl)benzoate $^1$H-NMR (400 MHz, DMSO-d$_6$): δ=3.92 (s, 3H), 3.94 (s, 3H), 7.03 (d, 1H), 7.71 (t, 1H), 8.19 (d, 1H), 8.29 (dd, 1H), 8.39 (d, 1H), 8.75 (s, 1H), 8.84 (d, 1H), 13.78 (s, 1H).

Intermediate 41: Methyl 5-(5-chloro-4-phenylthiazol-2-ylcarbamoyl)thiophene-2-carboxylate $^1$H-NMR (400 MHz, DMSO-d$_6$): δ=3.87 (s, 3H), 7.42 (t, 1H), 7.50 (t, 2H), 7.86 (d, 1H), 7.91 (d, 2H), 8.17 (d, 1H), 13.35 (s, 1H).

Intermediate 42: Methyl 3-(5-chloro-4-phenylthiazol-2-ylcarbamoyl)benzoate $^1$H-NMR (400 MHz, DMSO-d$_6$): δ=3.91 (d, 3H), 7.42 (t, 1H), 7.51 (t, 2H), 7.72 (dt, 1H), 7.93 (d, 2H), 8.21 (d, 1H), 8.36 (dd, 1H), 8.72 (s, 1H), 13.06 (s, 1H).

Intermediate 43: Methyl 5-(5-bromo-4-phenylthiazol-2-ylcarbamoyl)thiophene-2-carboxylate $^1$H-NMR (400 MHz, DMSO-d$_6$): δ=3.87 (s, 3H), 7.43 (t, 1H), 7.50 (t, 2H), 7.88 (dd, 3H), 8.23 (d, 1H), 13.41 (s, 1H).

Intermediate 44: Methyl 5-(5-fluoro-4-phenylthiazol-2-ylcarbamoyl)thiophene-2-carboxylate $^1$H-NMR (400 MHz, DMSO-d$_6$): δ=3.86 (s, 3H), 7.37 (d, 1H), 7.49 (t, 3H), 7.85 (d, 2H), 8.24 (d, 1H), 13.15 (s, 1H).

Intermediate 45: Methyl 5-(5-cyano-4-(pyridin-3-yl)thiazol-2-ylcarbamoyl)thiophene-2-carboxylate $^1$H-NMR (400 MHz, DMSO-d$_6$): δ=3.84 (s, 3H), 7.56 (dd, 1H), 7.68 (d, 1H), 7.75 (d, 1H), 8.35 (d, 1H), 8.64 (d, 1H), 9.19 (s, 1H).

Intermediate 46: Methyl 3-(5-bromo-4-phenylthiazol-2-ylcarbamoyl)benzoate $^1$H-NMR (400 MHz, DMSO-d$_6$): δ=3.92 (s, 3H), 7.44 (d, 1H), 7.51 (t, 2H), 7.70 (t, 1H), 7.91 (d, 2H), 8.18 (dd, 1H), 8.36 (m, 1H), 12.91 (s, 1H).

Intermediate 47: Methyl 3-(5-fluoro-4-phenylthiazol-2-ylcarbamoyl)benzoate $^1$H-NMR (400 MHz, DMSO-d$_6$): δ=7.38 (d, 1H), 7.50 (t, 2H), 7.70 (t, 2H), 7.86 (d, 2H), 8.18 (d, 1H), 8.36 (d, 1H), 8.71 (s, 1H), 12.99 (s, 1H).

Intermediate 48: Methyl 5-(5-chloro-4-(4-methoxyphenyl)thiazol-2-ylcarbamoyl)thiophene-2-carboxylate $^1$H-NMR (400 MHz, DMSO-d$_6$): δ=3.81 (s, 3H), 3.86 (s, 3H), 7.05 (d, 2H), 7.85 (dd, 3H), 8.13 (d, 1H), 13.39 (s, 1H).

EXAMPLES

Example 1: 3-[5-cyano-4-(3,4-dimethoxyphenyl)thiazol-2-ylcarbamoyl]benzoic Acid

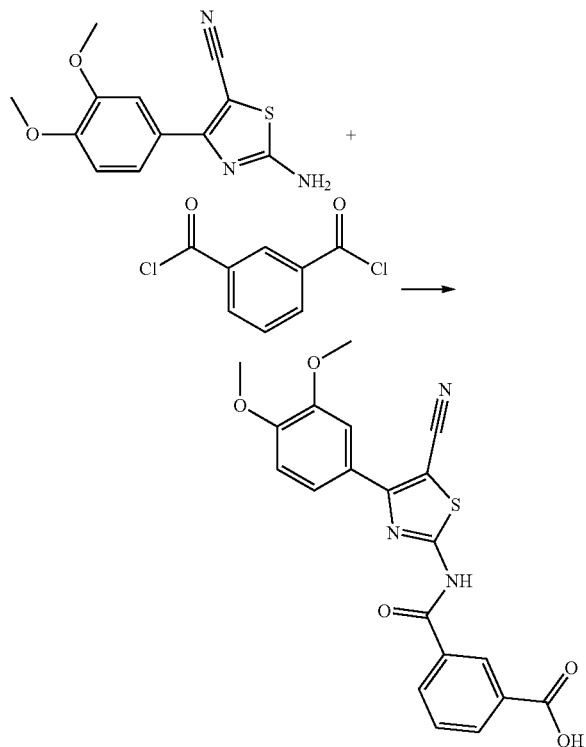

To a solution of 0.20 g (0.77 mmol) of 2-amino-4-(3,4-dimethoxyphenyl)thiazole-5-carbonitrile (Intermediate 10) in THF (4 ml), 0.2 ml of pyridine was added followed by a slow addition of 0.19 g (0.92 mmol) of isophthaloyl dichloride. The reaction mixture was stirred for 12 hours at room temperature. Then, 2 ml of water were added and the reaction was stirred an additional hour at room temperature. 5 ml of a solution of NaOH (1 M) were then added. The resulting solution is then stirred at room temperature for 2 hours and washed 3 times with DCM in a separating funnel. The desired acid precipitates by adding dropwise a solution of 4 M HCl until pH<3. The precipitate formed was filtered, washed with cold water and dried. 0.22 g (71.4%) of the desired product were obtained as a light brown solid.

$^1$H-NMR (400 MHz, DMSO-d$_6$): δ=3.84 (s, 3H), 3.86 (s, 3H), 7.19 (d, 1H), 7.61 (s, 1H), 7.66 (d, 1H), 7.71 (t, 1H), 8.21 (d, 1H), 8.36 (d, 1H), 8.72 (s, 1H), 13.73 (s, 1H).

The following examples were synthesized using the procedure described for Example 1, starting from the corresponding intermediate and acid chlorides in each case.

Example 2: 4-[5-cyano-4-(4-methoxyphenyl)thiazol-2-ylcarbamoyl]benzoic Acid $^1$H-NMR (400 MHz, DMSO-d$_6$): δ=3.82 (s, 3H), 7.12 (d, 2H), 8.00 (m, 3H), 8.07 (d, 2H), 8.21 (d, 2H), 13.71 (s, 1H).

Example 3: 4-[5-cyano-4-phenylthiazol-2-ylcarbamoyl]benzoic Acid $^1$H-NMR (400 MHz, DMSO-d$_6$): δ=7.58 (m, 3H), 8.05 (m, 3H), 8.11 (d, 2H), 8.24 (d, 2H), 13.76 (s, 1H).

Example 4: 3-(5-cyano-4-phenylthiazol-2-ylcarbamoyl)benzoic Acid $^1$H-NMR (400 MHz, DMSO-d$_6$): δ=7.59 (m, 4H), 7.73 (t, 1H), 8.05 (m, 2H), 8.22 (d, 1H), 8.38 (d, 1H), 8.74 (s, 1H), 13.80 (s, 1H).

Example 5: 6-(5-cyano-4-phenylthiazol-2-ylcarbamoyl)pyridine-2-carboxylic Acid $^1$H-NMR (400 MHz, DMSO-d$_6$): δ=7.59 (m, 3H), 8.06 (d, 2H), 8.36 (d, 1H), 8.39 (t, 1H), 8.47 (d, 1H), 13.28 (s, 1H), 13.79 (s, 1H).

Example 6: 3-(5-cyano-4-(4-methoxyphenyl)thiazol-2-ylcarbamoyl)benzoic Acid $^1$H-NMR (400 MHz, DMSO-d$_6$): δ=3.85 (s, 3H), 7.16 (d, 2H), 7.72 (t, 1H), 8.03 (d, 2H), 8.21 (d, 1H), 8.37 (d, 1H), 8.73 (s, 1H), 13.74 (s, 1H).

Example 7: 2-[5-cyano-4-(4-methoxyphenyl)thiazol-2-ylcarbamoyl]benzoic Acid $^1$H-NMR (400 MHz, DMSO-d$_6$): δ=3.82 (s, 3H), 7.11 (d, 2H), 7.66 (m, 3H), 7.96 (m, 3H), 8.46 (s, 1H), 13.45 (s, 1H).

Example 8: 5-(5-cyano-4-(4-methoxyphenyl)thiazol-2-ylcarbamoyl)thiophene-2-carboxylic Acid $^1$H-NMR (400 MHz, DMSO-d$_6$): δ=3.83 (s, 3H), 7.12 (d, 2H), 7.69 (d, 2H), 7.79 (d, 1H), 7.99 (d, 1H), 8.25 (s, 1H), 13.61 (s, 1H).

Example 9: 6-[5-cyano-4-(4-methoxyphenyl)thiazol-2-ylcarbamoyl]pyridine-2-carboxylic Acid $^1$H-NMR (400 MHz, DMSO-d$_6$): δ=3.85 (s, 3H), 7.14 (d, 2H), 8.03 (d, 2H), 8.35 (d, 1H), 8.38 (t, 1H), 8.46 (d, 1H), 13.28 (s, 1H), 13.73 (s, 1H).

Example 10: 3-{5-cyano-4-[4-(trifluoromethoxy)phenyl]thiazol-2-ylcarbamoyl}benzoic Acid $^1$H-NMR (400 MHz, DMSO-d$_6$): δ=7.59 (d, 2H), 7.70 (t, 1H), 8.14 (d, 2H), 8.19 (d, 1H), 8.37 (d, 1H), 8.71 (s, 1H), 13.49 (s, 1H).

Example 11: 5-{5-cyano-4-[4-(trifluoromethoxy)phenyl]thiazol-2-ylcarbamoyl}thiophene-2-carboxylic Acid $^1$H-NMR (400 MHz, DMSO-d$_6$): δ=7.58 (d, 2H), 7.79 (d, 1H), 8.12 (d, 2H), 8.26 (d, 1H), 8.24 (s, 1H), 13.60 (s, 1H).

Example 12: 3-[5-cyano-4-(4-fluorophenyl)thiazol-2-ylcarbamoyl]benzoic Acid $^1$H-NMR (400 MHz, DMSO-d$_6$): δ=7.44 (t, 2H), 732 (t, 1H), 8.09 (dd, 2H), 8.22 (d, 1H), 8.37 (d, 1H), 8.72 (s, 1H), 13.27 (s, 1H), 13.79 (s, 1H).

Example 13: 5-(5-cyano-4-(4-fluorophenyl)thiazol-2-ylcarbamoyl)thiophene-2-carboxylic Acid $^1$H-NMR (400 MHz, DMSO-d$_6$): δ=7.44 (t, 2H), 7.81 (d, 1H), 8.08 (dd, 2H), 8.30 (d, 1H), 13.81 (s, 2H).
HPLC-MS: Rt 3.073 m/z 374.1 (MH$^+$).

Example 14: 5-[5-cyano-4-(3-fluorophenyl)thiazol-2-ylcarbamoyl]thiophene-2-carboxylic Acid $^1$H-NMR (400 MHz, DMSO-d$_6$): δ=7.42 (s, 1H), 7.77 (m, 4H), 8.29 (s, 1H), 13.88 (s, 2H).
HPLC-MS: Rt 2.577 m/z 374.0 (MH$^+$).

Example 15: 5-(5-cyano-4-(2-fluorophenyl)thiazol-2-ylcarbamoyl)thiophene-2-carboxylic Acid $^1$H-NMR (400 MHz, DMSO-d$_6$): δ=7.43 (m, 2H), 7.63 (s, 1H), 7.79 (d, 2H), 8.28 (s, 1H), 13.85 (s, 2H).
HPLC-MS: Rt 2.265 m/z 374.0 (MH$^+$).

Example 16: 3-[5-cyano-4-(pyridin-4-yl)thiazol-2-ylcarbamoyl]benzoic Acid $^1$H-NMR (400 MHz, DMSO-d$_6$): δ=7.73 (t, 1H), 7.98 (d, 2H), 8.23 (d, 1H), 8.38 (d, 1H), 8.73 (s, 1H), 8.83 (d, 2H), 13.26 (s, 1H), 13.90 (s, 1H).

Example 17: 3-[5-cyano-4-(pyridin-2-yl)thiazol-2-ylcarbamoyl]benzoic Acid $^1$H-NMR (400 MHz, DMSO-d$_6$): δ=7.52 (t, 1H), 7.70 (t, 1H), 8.01 (t, 1H), 8.08 (d, 1H), 8.19 (d, 1H), 8.36 (d, 1H), 8.72 (s, 1H), 8.74 (d, 1H), 13.24 (s, 1H), 13.77 (s, 1H).

Example 18: 3-[5-cyano-4-(6-methylpyridin-2-yl)thiazol-2-ylcarbamoyl]benzoic Acid $^1$H-NMR (400 MHz, DMSO-d$_6$): δ=2.56 (s, 3H), 7.37 (d, 1H), 7.70 (t, 1H), 7.88 (m, 2H), 8.20 (d, 1H), 8.36 (d, 1H), 8.71 (s, 1H), 13.24 (s, 1H), 13.73 (s, 1H).

Example 19: 5-(5-cyano-4-(pyridin-3-yl)thiazol-2-ylcarbamoyl)thiophene-2-carboxylic Acid $^1$H-NMR (400 MHz, DMSO-d$_6$): δ=7.65 (dd, 1H), 7.81 (d, 1H), 8.30 (d, 1H), 8.37 (m, 1H), 8.74 (dd, 1H), 9.19 (d, 1H), 13.94 (s, 2H).
HPLC-MS: Rt 1.836 m/z 357.0 (MH$^+$).

Example 20: 5-(5-cyano-4-(3-cyanophenyl)thiazol-2-ylcarbamoyl)thiophene-2-carboxylic Acid $^1$H-NMR (400 MHz, DMSO-d$_6$): δ=7.82 (d, 1H), 7.86 (t, 1H), 8.08 (d, 1H), 8.22 (d, 1H), 8.31 (d, 1H), 8.35 (s, 1H), 13.80 (s, 2H).

Example 21: 5-(5-cyano-4-(4-cyanophenyl)thiazol-2-ylcarbamoyl)thiophene-2-carboxylic Acid $^1$H-NMR (400 MHz, DMSO-d$_6$): δ=7.80 (s, 1H), 8.08 (s, 2H), 8.21 (m, 3H), 13.82 (s, 2H).

Example 22: 5-(5-cyano-4-phenylthiazol-2-ylcarbamoyl)thiophene-2-carboxylic Acid

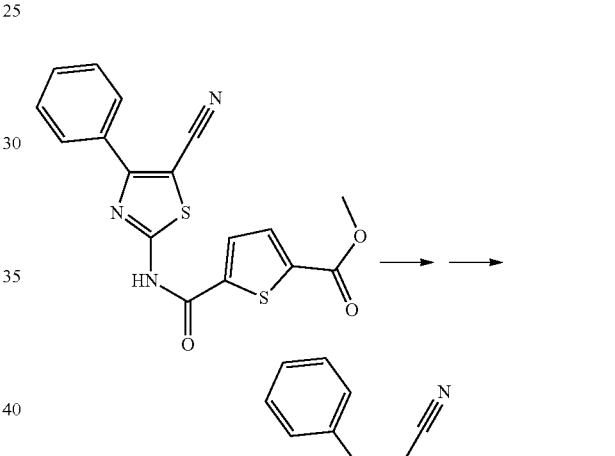

In a 50 mL vessel equipped with a stopcock at the bottom and a mechanical stirrer, 0.2 g of the corresponding methyl ester (Intermediate 25 in this case) were suspended in 3 mL of THF. To this suspension was then added slowly 5 mL of sodium hydroxide (1M). The dark solution obtained was stirred at room temperature until TLC indicates the disappearance of the starting material. Water (15 mL) and chloroform (30 mL) were then added and the biphasic system was stirred for 20 min. The phases were then separated and the aqueous phase was washed successively with chloroform (30 mL) and dichloromethane (30 mL). The aqueous phase was filtered to remove insoluble impurities.

Under a strong mechanical stirring, the resulting aqueous phase (initial pH of about 12) was acidified with hydrochloric acid 4 M to reach a pH<3. Already at pH=6, a brownish solid starts to precipitate. The suspension was stirred 30 min at room temperature and filtered. The solid was washed with 50 mL of water, and then 2 times more with 20 ml water at 60° C., and dried to obtain the title compound ¹H-NMR (400 MHz, DMSO-d₆): δ=7.59 (m, 3H), 7.71 (s, 1H), 7.82 (d, 1H), 8.03 (d, 2H), 8.29 (d, 1H), 13.88 (s, 1H).

The following examples were synthesized using the procedure described for Example 22, starting from the corresponding intermediates and carbonyl chlorides in each case.

Example 23: 5-(5-cyano-4-(6-methoxypyridin-3-yl) thiazol-2-ylcarbamoyl)thiophene-2-carboxylic Acid ¹H-NMR (400 MHz, DMSO-d₆): δ=3.93 (s, 3H), 7.02 (d, 1H), 7.78 (d, 1H), 8.26 (dd, 2H), 8.80 (d, 1H), 13.85 (s, 2H).
HPLC-MS: Rt 2.189 m/z 387.0 (MH⁺).

Example 24: 5-((5-cyano-4-(furan-2-yl)thiazol-2-yl) carbamoyl)thiophene-2-carboxylic Acid ¹H-NMR (400 MHz, DMSO-d₆): δ=6.76 (dd, 1H), 7.11 (dd, 1H), 7.81 (d, 1H), 7.99-8.02 (m, 1H), 8.29 (d, 1H), 13.94 (s, 2H).
HPLC-MS: Rt 2.083, m/z 346.0 (MH⁺).

Example 25: 5-((5-cyano-4-(thiophen-2-yl)thiazol-2-yl)carbamoyl)thiophene-2-carboxylic Acid ¹H-NMR (400 MHz, DMSO-d₆): δ=7.28 (dd, 1H), 7.80 (d, 1H), 7.83 (dd, 1H) 7.91 (dd, 1H), 8.29 (d, 1H), 13.87 (s, 2H).
HPLC-MS: Rt 2.362, m/z 362.0 (MH⁺).

Example 26: 5-((4-(4-chlorothiophen-2-yl)-5-cyanothiazol-2-yl)carbamoyl)thiophene-2-carboxylic Acid ¹H-NMR (400 MHz, DMSO-d₆): δ=7.71 (s, 1H), 7.78 (d, 1H), 7.86 (s, 1H), 8.24 (d, 1H), 13.80 (s, 2H).

Example 27: 5-((5'-cyano-[2,4'-bithiazol]-2'-yl)carbamoyl)thiophene-2-carboxylic Acid ¹H-NMR (400 MHz, DMSO-d₆): δ=7.81 (d, 1H), 8.03 (d, 1H), 8.12 (d, 1H), 8.29 (d, 1H), 13.95 (s, 2H).
HPLC-MS: Rt 1.916, m/z 363.0 (MH⁺).

Example 28: 3-((5'-cyano[2,4'-bithiazol]-2'-yl)carbamoyl)benzoic Acid

¹H-NMR (400 MHz, DMSO-d₆): δ=7.72 (t, 1H), 8.04 (d, 1H), 8.13 (d, 1H), 8.22 (d, 1H), 8.37 (d, 1H), 8.73 (s, 1H), 13.36 (s, 1H), 13.91 (s, 1H).
HPLC-MS: Rt 2.129, m/z 357.0 (MH⁺).

Example 29: 4-((5'-cyano[2,4'-bithiazol]-2'-yl)carbamoyl)benzoic Acid

¹H-NMR (400 MHz, DMSO-d₆): δ=8.04 (d, 1H), 8.09 (d, 2H), 8.13 (d, 1H), 8.24 (d, 2H), 13.41 (s, 1H), 13.88 (s, 1H).
HPLC-MS: Rt 2.049, m/z 357.0 (MH⁺).

Example 30: 4-((5-cyano-4-(thiophen-2-yl)thiazol-2-yl)carbamoyl)benzoic Acid

¹H-NMR (400 MHz, DMSO-d₆): δ=7.29 (dd, J=5.0, 3.8 Hz, 1H), 7.88-7.82 (m, 1H), 7.92 (dd, J=3.7, 1.0 Hz, 1H), 8.09 (d, J=8.5 Hz, 2H), 8.24 (d, J=8.5 Hz, 2H), 13.44 (s, 1H), 13.80 (s, 1H).
HPLC-MS: Rt 2.589, m/z 356.0 (MH⁺).

Example 31: 3-((5-cyano-4-(thiophen-2-yl)thiazol-2-yl)carbamoyl)benzoic Acid

¹H-NMR (400 MHz, DMSO-d₆): δ=7.29 (dd, 1H), 7.72 (t, 1H), 7.85 (dd, 1H), 7.93 (dd, 1H), 8.20-8.24 (m, 1H), 8.35-8.40 (m, 1H), 8.72 (t, 1H), 13.32 (s, 2H), 13.81 (s, 1H).

Example 32: 3-((5-cyano-4-(furan-2-yl)thiazol-2-yl) carbamoyl)benzoic Acid

¹H-NMR (400 MHz, DMSO-d₆): δ=6.76 (dd, 1H), 7.11 (dd, 1H), 7.71 (t, 1H), 8.00 (dd, 1H), 8.21 (dt 1H), 8.34-8.39 (m, 1H), 8.71 (t, 1H), 13.35 (s, 1H) 13.84 (s, 1H).

Example 33: 4-((5-cyano-4-(furan-2-yl)thiazol-2-yl) carbamoyl)benzoic Acid

¹H-NMR (400 MHz, DMSO-d₆): δ=6.76 (ddd, 1H), 7.10 (dt, 1H), 7.99 (dd, 1H), 8.12-8.05 (2, 1H), 8.25-8.20 (m, 2H), 13.64 (m, 2H).

Example 34: 3-((4-(4-chlorothiophen-2-yl)-5-cyanothiazol-2-yl)carbamoyl)benzoic Acid ¹H-NMR (400 MHz, DMSO-d₆): δ=7.71 (dd, 2H), 7.88 (s, 1H), 8.21 (d, 1H), 8.35 (d, 1H), 8.71 (s, 1H), 13.36 (s, 1H), 13.83 (s, 1H).

Example 35: 4-((4-(4-chlorothiophen-2-yl)-5-cyanothiazol-2-yl)carbamoyl)benzoic Acid ¹H-NMR (400 MHz, DMSO-d₆): δ=7.74 (s, 1H), 7.88 (s, 1H), 8.08 (d, 2H), 8.22 (d, 2H), 13.40 (s, 1H), 13.80 (s, 1H).

Example 36: 5-((5-cyano-4-(3-methoxyphenyl)thiazol-2-yl)carbamoyl)thiophene-2-carboxylic Acid ¹H-NMR (400 MHz, DMSO-d₆): δ=3.83 (s, 3H), 7.13 (m, 2H), 7.51 (t, 1H), 7.58 (d, Hz, 1H), 7.63 (d, Hz, 1H), 7.81 (d, 1H), 13.90 (s, 2H).

Example 37: 3-(5-cyano-4-(6-methoxypyridin-3-yl) thiazol-2-ylcarbamoyl)benzoic Acid ¹H-NMR (400 MHz, DMSO-d₆): δ=3.94 (s, 3H), 7.04 (d, 1H), 7.71 (t, 1H), 8.21 (d, 1H), 8.29 (dd, 1H), 8.36 (d, 1H), 8.72 (s, 1H), 8.84 (d, 1H), 13.34 (s, 1H), 13.80 (s, 1H).
HPLC-MS: Rt 2.419 m/z 381.0 (MH⁺).

Example 38: 5-(5-chloro-4-phenylthiazole-2-ylcarbamoyl)thiophene-2-carboxylic Acid ¹H-NMR (400 MHz, DMSO-d₆): δ=7.43 (m, 1H), 7.51 (t, 2H), 7.79 (d, 1H), 7.91 (d, 2H), 8.25 (d, 1H), 13.38 (s, 1H), 13.64 (s, 1H).
HPLC-MS: Rt 3.088 m/z 364.9 (M⁺).

Example 39: 3-(5-chloro-4-phenylthiazole-2-ylcarbamoyl)benzoic Acid

¹H-NMR (400 MHz, DMSO-d₆): δ=7.43 (t, 1H), 7.52 (t, 2H), 7.70 (t, 1H), 7.93 (d, 2H), 8.19 (d, 1H), 8.35 (d, 1H), 8.69 (s, 1H), 13.27 (s, 2H).
HPLC-MS: Rt 3.178 m/z 359.0 (MH⁺).

Example 40: 5-(5-bromo-4-phenylthiazol-2-ylcarbamoyl)thiophene-2-carboxylic Acid $^1$H-NMR (400 MHz, DMSO-d$_6$): δ=7.44 (d, 1H), 7.50 (t, 2H), 7.79 (d, 1H), 7.90 (d, 2H), 8.25 (d, 1H), 13.40 (s, 1H), 13.64 (s, 1H).
HPLC-MS: Rt 3.118 m/z 410.9 (MH$^+$).

Example 41: 5-(5-fluoro-4-phenylthiazol-2-ylcarbamoyl)thiophene-2-carboxylic Acid $^1$H-NMR (400 MHz, DMSO-d$_6$): δ=7.39 (d, 1H), 7.51 (t, 2H), 7.79 (d, 1H), 7.84 (d, 2H), 8.24 (d, 1H), 13.18 (s, 1H), 13.63 (s, 1H).
HPLC-MS: Rt 3.012 m/z 349.0 (MH$^+$).

Example 42: 3-(5-bromo-4-phenylthiazol-2-ylcarbamoyl)benzoic Acid $^1$H-NMR (400 MHz, DMSO-d$_6$): δ=7.44 (d, 1H), 7.51 (t, 2H), 7.70 (t, 1H), 7.91 (d, 2H), 8.18 (dd, 1H), 8.35 (d, 1H), 8.69 (s, 1H), 13.29 (s, 2H).
HPLC-MS: Rt 3.221 m/z 405.0 (MH$^+$).

Example 43: 3-(5-fluoro-4-phenylthiazole-2-ylcarbamoyl)benzoic Acid $^1$H-NMR (400 MHz, DMSO-d$_6$): b=7.39 (d, 1H), 7.51 (t, 2H), 7.70 (t, 1H), 7.86 (d, 2H), 8.18 (dd, 1H), 8.33 (d, 1H), 8.68 (s, 1H), 13.06 (s, 1H), 13.25 (s, 1H).
HPLC-MS: Rt 3.093 m/z 343.0 (MH$^+$).

Example 44: 5-(5-chloro-4-(4-methoxyphenyl)thiazol-2-ylcarbamoyl)thiophene-2-carboxylic Acid $^1$H-NMR (400 MHz, DMSO-d$_6$): δ=3.81 (s, 3H), 7.07 (d, 2H), 7.79 (d, 1H), 7.87 (d, 2H), 8.24 (d, 1H), 13.33 (s, 1H), 13.65 (s, 1H).
HPLC-MS: Rt 3.110 m/z 395.0 (MH$^+$).

Example 45: 5-[5-cyano-4-(4-methoxyphenyl)thiazol-2-ylcarbamoyl]-1H-pyrazole-3-carboxylic Acid

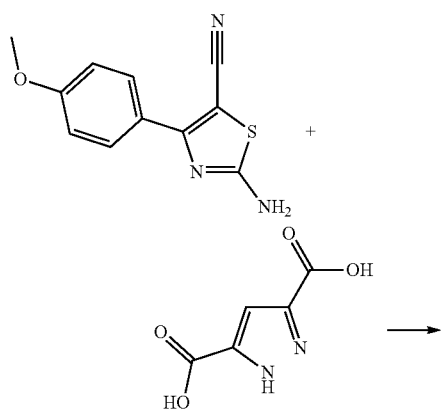

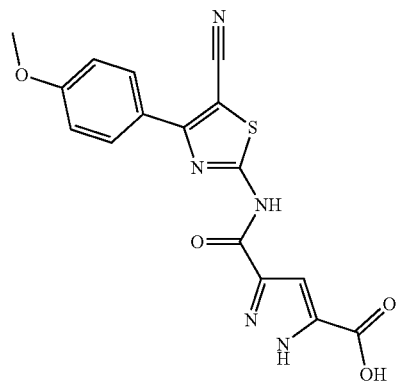

0.2 g (0.86 mmol) of 2-amino-4-(4-methoxyphenyl)thiazole-5-carbonitrile (Intermediate 9), 0.2 g (1.12 mmol) of 1H-pyrazole 3,5-dicarboxylic acid, 0.5 g (1.3 mmol) of HATU and 300 µl (1.7 mmol) of ethyldiisopropylamine were mixed in 20 ml of acetonitrile and stirred for 6 h at 90° C. After this time the solvent was removed under reduced pressure, and 5 ml of a solution of 1M sodium hydroxide were added and the organic impurities were filtered. The aqueous phase was extracted 3 times with DCM in a separating funnel and added 4M HCl dropwise until pH<3. The precipitate formed was filtered, washed with cold water and dried. 0.19 g (61.2%) of the desired product is obtained.

$^1$H-NMR (400 MHz, DMSO-d$_6$): δ=3.84 (s, 3H), 7.15 (d, 2H), 7.61 (s, 1H), 8.02 (d, 2H), 13.45 (s, 1H), 14.73 (s, 1H).

Example 46: 1-{3-[(5-cyano-4-phenyl-thiazol-2-yl)carbamoyl]benzoyl}piperidine-4-carboxylic Acid

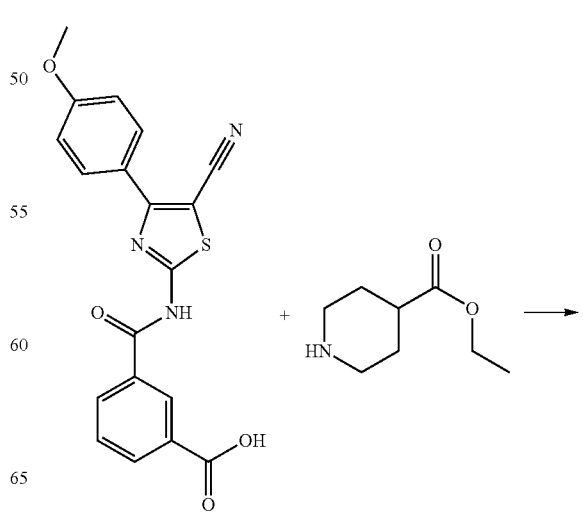

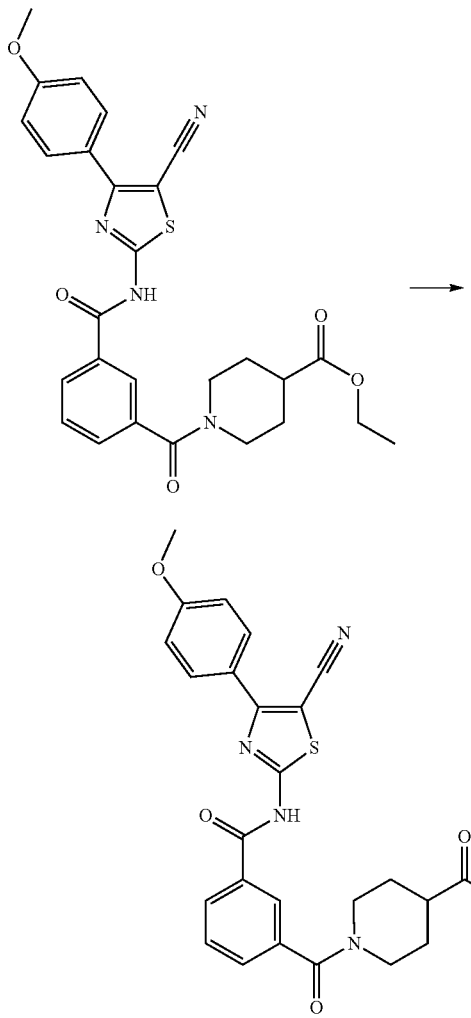

A mixture of 0.11 g (0.29 mmol) of 3-[5-cyano-4-(4-methoxyphenyl)thiazol-2-ylcarbamoyl) benzoic acid (Example 6), 49 μl (0.32 mmol) of ethyl piperidine-4-carboxylate, 0.13 g (0.34 mmol) of HATU and 60 μl (0.43 mmol) of TEA in 4 ml acetonitrile was allowed to react 24 h at room temperature. Then poured into cold water, the precipitate formed was filtered, washed several times with cold water and dried. Then the solid obtained was suspended in a solution of NaOH (5 mL, 1M) and stirred at room temperature following the reaction by thin layer chromatography (TLC) until the ester was completely hydrolyzed. The aqueous phase was then washed 3 times with DCM in a separating funnel. The phases were separated, and to the aqueous layers 4 M HCl was added until reaching pH<3. The precipitate formed was filtered, washed with cold water and dried. 0.083 g (58.4%) of the desired product is obtained as a light brown solid.

$^1$H-NMR (400 MHz, DMSO-d$_6$): δ=1.55 (m, 2H), 1.87 (m, 2H), 2.54 (m, 1H), 3.08 (m, 2H), 3.45 (m, 1H), 3.82 (s, 3H), 4.36 (m, 1H), 7.12 (d, 2H), 7.65 (m, 2H), 8.00 (d, 2H), 8.16 (m, 2H), 13.70 (s, 1H).

The following examples were synthesized using the procedure described for Example 46 from their corresponding starting materials:

Example 47: 1-{4-[(5-cyano-4-phenylthiazol-2-yl)carbamoyl]benzoyl}piperidine-4-carboxylic Acid $^1$H-NMR (400 MHz, DMSO-d$_6$): δ=1.56 (m, 2H), 1.87 (m, 2H), 2.55 (m, 1H), 3.08 (m, 2H), 3.45 (m, 1H), 4.37 (m, 1H), 7.54 (m, 3H), 7.98 (m, 2H), 8.18 (d, 2H), 8.37 (d, 2H), 8.45 (s, 1H), 13.51 (s, 1H).

Example 48: 1-{3-[(5-cyano-4-phenylthiazol-2-yl)carbamoyl]benzoyl}piperidine-4-carboxylic Acid $^1$H-NMR (400 MHz, DMSO-d$_6$): δ=1.55 (m, 2H), 1.88 (m, 2H), 2.54 (m, 1H), 3.08 (m, 2H), 3.45 (m, 1H), 4.36 (m, 1H), 7.54 (m, 3H), 7.69 (t, 1H), 7.99 (m, 2H), 8.31 (d, 1H), 8.40 (d, 1H), 8.45 (s, 1H), 8.86 (s, 1H), 13.51 (s, 1H).

Example 49: 1-(5-((5-cyano-4-phenylthiazol-2-yl)carbamoyl)thiophene-2-carbonyl)piperidine-4-carboxylic Acid $^1$H-NMR (400 MHz, DMSO-d$_6$): δ=1.55 (q, 2H), 1.89 (m, 2H), 2.55 (m, 1H), 3.16 (m, 2H), 3.17 (m, 2H), 4.10 (m, 1H), 7.51 (d, 1H), 7.55 (m, 3H), 7.99 (m, 2H), 8.29 (d, 1H), 12.33 (s, 1H), 13.79 (s, 1H).

HPLC-MS: Rt 2.394, m/z 467.1 (MH$^+$)

Example 50: 1-(4-((5-cyano-4-(thiophen-2-yl)thiazol-2-yl)carbamoyl)benzoyl)piperidine-4-carboxylic Acid $^1$H-NMR (400 MHz, DMSO-d$_6$): δ=1.77 (s, 1H), 1.92 (s, 1H), 1.53 (s, 2H), 2.50 (s, 1H), 2.97 (s, 1H), 3.12 (s, 1H), 3.45 (s, 1H), 4.34 (d, 1H), 7.29 (dd, 1H), 7.57 (d, 2H), 7.84 (dd, 1H), 7.92 (dd, 1H), 8.20 (m, 2H), 12.35 (2, 1H), 13.76 (s, 1H).

HPLC-MS: Rt 2.579, m/z 467.0 (MH$^+$).

Example 51: 1-(5-((5-cyano-4-(thiophen-2-yl)thiazol-2-yl)carbamoyl)thiophene-2-carbonyl)piperidine-4-carboxylic Acid $^1$H-NMR (400 MHz, DMSO-d$_6$): δ=1.56 (q, 2H), 1.90 (d, 2H), 2.58 (m, 1H), 3.17 (m, 2H), 4.09 (m, 2H), 7.33-7.26 (m, 1H), 7.50 (d, 1H), 7.84 (dd, 1H), 7.92 (dd, 1H), 8.28 (d, 1H), 12.35 (s, 1H), 13.81 (s, 1H).

Example 52: 1-(3-((5-cyano-4-(thiophen-2-yl)thiazol-2-yl)carbamoyl)benzoyl)piperidine-4-carboxylic Acid $^1$H-NMR (400 MHz, DMSO-d$_6$): δ=1.55 (d, 2H), 1.78 (s, 1H), 1.93 (s, 1H), 2.53-2.62 (m, 1H), 2.99 (s, 1H), 4.35 (s, 1H), 3.15 (s, 1H), 3.54 (s, 1H), 7.29 (dd, 1H), 7.62-7.72 (m, 2H), 7.84 (dd, 1H), 7.92 (dd, 1H), 8.19 (d, 2H), 12.35 (s, 1H), 13.69 (s, 1H).

The invention claimed is:
1. A compound of formula (I)

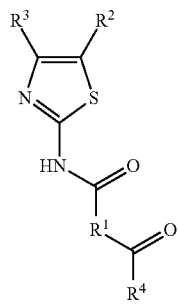

wherein:
R$^1$ represents a five or six membered aryl or heteroaryl group optionally substituted by one or more substituents selected from the group consisting of halogen atom, C$_1$-C$_6$ alkyl linear or branched, C$_3$-C$_{12}$ cycloalkyl, hydroxyl, C$_1$-C$_6$ alkoxy linear or branched and cyano group,
R$^2$ is selected from the group consisting of halogen atom and cyano group,
R$^3$ represents a five or six membered aryl or heteroaryl group optionally substituted by one or more substituents selected from the group consisting of halogen atom, cyano group, C$_3$-C$_{12}$ cycloalkyl, hydroxyl, C$_1$-C$_6$ alkoxy linear or branched, optionally substituted by one, two or three halogen atoms, C$_1$-C$_6$ alkylthio, amino, mono or dialkylamino, C$_1$-C$_6$ alcoxyalkyl, hydroxycarbonyl and C$_2$-C$_6$ alcoxycarbonyl, and
R$^4$ represents independently:
a) a hydroxyl group,
b) —N(R$^5$)(R$^6$) group, wherein:
i) R$^5$ and R$^6$ represent independently a C$_3$-C$_{12}$ cycloalkyl group or C$_3$-C$_4$ alkyl linear or branched, substituted by a carboxyl group (—COOH); or
ii) R$^5$ and R$^6$ form together with the nitrogen atom to which they are bound a five or six membered saturated cycle comprising optionally a heteroatom selected from N and O, which is substituted by a carboxylic group (—COOH),
and pharmaceutically acceptable salts thereof.

2. A compound according to claim 1 wherein R$^3$ represents a phenyl group optionally substituted by one, two or three halogen atoms or by a C$_1$-C$_6$ alkoxy group optionally substituted by one, two or three halogen atoms.

3. A compound according to claim 2 wherein R' is selected from a group consisting of phenyl group and thienyl group optionally substituted by one, two or three halogen atoms.

4. A compound according to claim 3 wherein R$^2$ represents a cyano group.

5. A compound according to claim 4 wherein R$^4$ represents a hydroxyl group.

6. A compound according to claim 4 wherein R$^4$ represents a —N(R$^5$)(R$^6$) group wherein:
i) R$^5$ and R$^6$ represent independently a C$_3$-C$_{12}$ cycloalkyl group or C$_3$-C$_4$ alkyl linear or branched, substituted by a carboxyl group (—COOH); or
ii) R$^5$ and R$^6$ form together with the nitrogen atom to which they are bound a five or six membered saturated cycle comprising optionally a heteroatom selected from N and O, which is substituted by a carboxylic group (—COOH).

7. A compound according to claim 6 wherein R$^5$ and R$^6$ form together with the nitrogen atom to which they are attached a five or six membered saturated cycle substituted by a carboxylic group (—COOH).

8. A compound according to claim 1 wherein R$^1$ represents a phenyl group optionally substituted by one, two or three halogen atoms, R$^2$ represents a cyano group, R$^3$ represents a phenyl group optionally substituted by one, two or three halogen atoms or by a methoxyl group, and R$^4$ represents a hydroxyl group.

9. A compound according to claim 1 wherein R$^1$ represents a thienyl group optionally substituted by one, two or three halogen atoms, R$^2$ represents a cyano group, R$^3$ represents a phenyl group optionally substituted by one, two or three halogen atoms or by a methoxyl group, and R$^4$ represents a hydroxyl group.

10. A compound according to claim 1 which is one of:
3-[5-cyano-4-(3,4-dimethoxyphenyl)thiazol-2-ylcarbamoyl]benzoic acid;
4-[5-cyano-4-(4-methoxyphenyl)thiazol-2-ylcarbamoyl]benzoic acid;
4-(5-cyano-4-phenylthiazol-2-ylcarbamoyl)benzoic acid;
3-(5-cyano-4-phenylthiazol-2-ylcarbamoyl)benzoic acid;
6-(5-cyano-4-phenylthiazol-2-ylcarbamoyl)pyridine-2-carboxylic acid;
3-(5-cyano-4-(4-methoxyphenyl)thiazol-2-ylcarbamoyl)benzoic acid;
2-[5-cyano-4-(4-methoxyphenyl)thiazol-2-ylcarbamoyl]benzoic acid;
5-(5-cyano-4-(4-methoxyphenyl)thiazol-2-ylcarbamoyl)thiophene-2-carboxylic acid;
6-[5-cyano-4-(4-methoxyphenyl)thiazol-2-ylcarbamoyl]pyridine-2-carboxylic acid;
3-{5-cyano-4-[4-(trifluoromethoxy)phenyl]thiazol-2-ylcarbamoyl}benzoic acid;
5-{5-cyano-4-[4-(trifluoromethoxy)phenyl]thiazol-2-ylcarbamoyl}thiophene-2-carboxylic acid;
3-[5-cyano-4-(4-fluorophenyl)thiazol-2-ylcarbamoyl]benzoic acid;
5-(5-cyano-4-(4-fluorophenyl)thiazol-2-ylcarbamoyl)thiophene-2-carboxylic acid;
5-[5-cyano-4-(3-fluorophenyl)thiazol-2-ylcarbamoyl]thiophene-2-carboxylic acid;
5-(5-cyano-4-(2-fluorophenyl)thiazol-2-ylcarbamoyl)thiophene-2-carboxylic acid;
3-[5-cyano-4-(pyridin-4-yl)thiazol-2-ylcarbamoyl]benzoic acid;
3-[5-cyano-4-(pyridin-2-yl)thiazol-2-ylcarbamoyl]benzoic acid;
3-[5-cyano-4-(6-methylpyridin-2-yl)thiazol-2-ylcarbamoyl]benzoic acid;
5-(5-cyano-4-(pyridin-3-yl)thiazol-2-ylcarbamoyl)thiophene-2-carboxylic acid;
5-(5-cyano-4-(3-cyanophenyl)thiazol-2-ylcarbamoyl)thiophene-2-carboxylic acid;
5-(5-cyano-4-(4-cyanophenyl)thiazol-2-ylcarbamoyl)thiophene-2-carboxylic acid;
5-(5-cyano-4-phenylthiazol-2-ylcarbamoyl)thiophene-2-carboxylic acid;
5-(5-cyano-4-(6-methoxypyridin-3-yl)thiazol-2-ylcarbamoyl)thiophene-2-carboxylic acid;
5-((5-cyano-4-(furan-2-yl)thiazol-2-yl)carbamoyl)thiophene-2-carboxylic acid;
5-((5-cyano-4-(thiophen-2-yl)thiazol-2-yl)carbamoyl)thiophene-2-carboxylic acid;
5-((4-(4-chlorothiophen-2-yl)-5-cyanothiazol-2-yl)carbamoyl)thiophene-2-carboxylic acid;

5-((5'-cyano-[2,4'-bithiazol]-2'-yl)carbamoyl)thiophene-2-carboxylic acid;
3-((5'-cyano-[2,4'-bithiazol]-2'-yl)carbamoyl)benzoic acid;
4-((5'-cyano-[2,4'-bithiazol]-2'-yl)carbamoyl)benzoic acid;
4-((5-cyano-4-(thiophen-2-yl)thiazol-2-yl)carbamoyl)benzoic acid;
3-((5-cyano-4-(thiophen-2-yl)thiazol-2-yl)carbamoyl)benzoic acid;
3-((5-cyano-4-(furan-2-yl)thiazol-2-yl)carbamoyl)benzoic acid;
4-((5-cyano-4-(furan-2-yl)thiazol-2-yl)carbamoyl)benzoic acid;
3-((4-(4-chlorothiophen-2-yl)-5-cyanothiazol-2-yl)carbamoyl)benzoic acid;
4-((4-(4-chlorothiophen-2-yl)-5-cyanothiazol-2-yl)carbamoyl)benzoic acid;
5-((5-cyano-4-(3-methoxyphenyl)thiazol-2-yl)carbamoyl)thiophene-2-carboxylic acid;
3-(5-cyano-4-(6-methoxypyridin-3-yl)thiazol-2-ylcarbamoyl)benzoic acid;
5-(5-chloro-4-phenylthiazole-2-ylcarbamoyl)thiophene-2-carboxylic acid;
3-(5-chloro-4-phenylthiazole-2-ylcarbamoyl)benzoic acid;
5-(5-bromo-4-phenylthiazol-2-ylcarbamoyl)thiophene-2-carboxylic acid;
5-(5-fluoro-4-phenylthiazol-2-ylcarbamoyl)thiophene-2-carboxylic acid;
3-(5-bromo-4-phenylthiazol-2-ylcarbamoyl)benzoic acid;
3-(5-fluoro-4-phenylthiazole-2-ylcarbamoyl)benzoic acid;
5-(5-chloro-4-(4-methoxyphenyl)thiazol-2-ylcarbamoyl)thiophene-2-carboxylic acid;
5-[5-cyano-4-(4-methoxyphenyl)thiazol-2-ylcarbamoyl]-1H-pyrazole-3-carboxylic acid;
1-(3-{[5-cyano-4-(4-methoxyphenyl)thiazol-2-yl]carbamoyl}benzoyl)piperidine-4-carboxylic acid;
1-{4-[(5-cyano-4-phenyl-thiazol-2-yl)carbamoyl]benzoyl}piperidine-4-carboxylic acid;
1-{3-[(5-cyano-4-phenyl-thiazol-2-yl)carbamoyl]benzoyl}piperidine-4-carboxylic acid;
1-(5-((5-cyano-4-phenylthiazol-2-yl)carbamoyl)thiophene-2-carbonyl)piperidine-4-carboxylic acid;
1-(4-((5-cyano-4-(thiophen-2-yl)thiazol-2-yl)carbamoyl)benzoyl)piperidine-4-carboxylic acid;
1-(5-((5-cyano-4-(thiophen-2-yl)thiazol-2-yl)carbamoyl)thiophene-2-carbonyl)piperidine-4-carboxylic acid; and
1-(3-((5-cyano-4-(thiophen-2-yl)thiazol-2-yl)carbamoyl)benzoyl)piperidine-4-carboxylic acid.

11. A pharmaceutical composition comprising a compound of claim 1 or pharmaceutically acceptable salt thereof and a pharmaceutically acceptable diluent or carrier.

12. Method for the treatment of a disease or pathological condition susceptible of amelioration by modulation of the adenosine $A_3$ receptor, said method comprising administering to a subject in need thereof an effective amount of a compound according to claim 1, wherein the disease or pathological condition susceptible of amelioration by modulation of the adenosine $A_3$ receptor is selected from the group consisting of: atherosclerosis; asthma; autoimmune diseases selected from rheumatoid arthritis and psoriasis, diseases of the gastrointestinal system selected from ulcerative colitis, Crohn's disease, and inflammatory bowel disease; and ophthalmologic diseases selected from glaucoma and uveitis.

13. A combination comprising a compound of claim 1 and a therapeutic agent used for the treatment of diseases selected from the group consisting of neurological disorders, cardiovascular diseases, respiratory diseases, renal diseases, cancer, autoimmune diseases, diseases of the gastrointestinal system, and phthalmologic diseases or conditions.

14. A combination comprising a compound of claim 1 and a therapeutic agent selected from the group consisting of Montelukast, Bicalutamide, Flutamide, Tofacitinib, and a diuretic selected from Hydrochlorothiazide and Lubiprostone for the treatment of a disease selected from glaucoma, asthma, prostate cancer, rheumatoid arthritis, acute renal failure and irritable bowel syndrome.

* * * * *